us (12) United States Patent
Kendrew et al.

(10) Patent No.: US 7,807,800 B2
(45) Date of Patent: Oct. 5, 2010

(54) ERYTHROMYCINS AND PROCESS FOR THEIR PREPARATION

(75) Inventors: Steven Gary Kendrew, Little Chesterford (GB); Rachel E. Lill, Little Chesterford (GB)

(73) Assignee: Biotica Technology Limited, Cambridge (GB)

( * ) Notice: Subject to any disclaimer, the term of this patent is extended or adjusted under 35 U.S.C. 154(b) by 287 days.

(21) Appl. No.: 10/580,781

(22) PCT Filed: Nov. 29, 2004

(86) PCT No.: PCT/GB2004/005018

§ 371 (c)(1),
(2), (4) Date: Jun. 13, 2007

(87) PCT Pub. No.: WO2005/054266

PCT Pub. Date: Jun. 16, 2005

(65) Prior Publication Data

US 2007/0299252 A1 Dec. 27, 2007

(30) Foreign Application Priority Data

Nov. 28, 2003 (GB) ................................ 0327720.9

(51) Int. Cl.
*C07H 17/08* (2006.01)
(52) U.S. Cl. ....................................... 536/7.2
(58) Field of Classification Search .................. 536/7.2
See application file for complete search history.

(56) References Cited

U.S. PATENT DOCUMENTS 4,429,115 A    1/1984    Cappelletti et al.
6,147,197 A  * 11/2000    Or et al. ....................... 536/7.2
2003/0203425 A1  10/2003  Leadlay et al.

FOREIGN PATENT DOCUMENTS

FR        2754821         4/1998

OTHER PUBLICATIONS

Spagnoli, R. et al., "Biological conversion of erythronolide B, an intermediate of erythromycin biogenesis, into new hybrid macrolide antibiotics", Journal of Antibiotics, 36: 365-375 (1983).
Mochizuki, S. et al., "The large linear plasmid pSLA2-L of *Streptomyces rochei* had an unusually condensed gene organization for secondary metabolism", Molecular Microbiology, 48(6): 1501-1510 (2003).
Gaisser, S. et al., "Parallel pathways for oxidation of 14-membered polyketide macrolactones in *Saccharopolyspora erythraea*", Molecular Microbiology, 44(3): 771-781 (2002).
Ferrero, J. et al., "Metabolism and Disposition of Clarithromycin in Man", Drug Metabolism and Disposition, 18(4): 441-446 (1990).
Omura, S. et al., "Antibacterial Activity of Some Acetyl Derivatives of Kujimycin A", The Journal of Antibiotics, 24(10): 717-718 (1971).

* cited by examiner

*Primary Examiner*—Elli Peselev
(74) *Attorney, Agent, or Firm*—J. Michael Strickland

(57) ABSTRACT

14-membered macrolide compounds such as erythromycins are provided with functional groups at the 14- and/or 15-position by providing a 14-membered aglycone template and feeding it to a strain capable of hydroxylating it at the 14 and/or 15 position. The strain may be found by screening, selected from known strains (e.g. *Streptomyces eurythermus* DSM 40014) or produced by genetically engineering a strain to express a cytochrome P450 enzyme.

6 Claims, 3 Drawing Sheets

14 OH-EB
HMBC H⟶C

15 OH-EB
HMBC H→ C

ERYTHROMYCINS AND PROCESS FOR THEIR PREPARATION

The present application is §371 application of PCT/GB2004/005018 filed Nov. 29, 2004 which claims priority to GB application No. 0327720.9 filed Nov. 28, 2003, the entire disclosure of each being incorporated by reference herein.

The present invention is directed to compositions and methods for producing a range of 14-membered macrolides; particularly including erythronolides and erythromycins.

BACKGROUND OF THE INVENTION

Erythromycins are members of the polyketide class of natural products that also includes many important antibiotic, antifungal, anticancer, and immunosuppressive compounds (Staunton and Wilkinson Chem. Rev. (1997) 97, 2611-2629). This class of compounds has attracted considerable interest because of the wide range of biological activities these compounds possess, and their potential to provide therapeutic drugs across a wide range of disease states.

More recently the discovery that these compounds are synthesised by the repeated stepwise condensation of acyl-thioesters in a manner analogous to that of fatty acid biosynthesis to generate chains of varying length and substitution has attracted research towards uncovering the enzymic mechanisms by which these molecules are put together. FIG. 1 shows how erythromycin is assembled from these basic ketide units. The structural diversity found among natural polyketides arises in part from the selection of (usually) acetate (malonyl-CoA) or propionate (methylmalonyl-CoA) as "starter" or "extender" units (although one of a variety of other types of unit may occasionally be selected). Further structural diversity is given by the differing degree of processing of the β-keto group formed after each condensation. Examples of processing steps include reduction to β-hydroxyacyl-, reduction followed by dehydration to 2-enoyl-, and complete reduction to the saturated acyl-thioester. The stereochemical outcome of these processing steps is also specified for each cycle of chain extension. Methylation at the α-carbon or at the oxygen substituent is also sometimes observed. These processes are catalysed and controlled by a polyketide synthase. Other enzymes add further structural diversity after the completed polyketide chain is released from the PKS, for example, methylation, oxidation or glycosylation. A number of types of polyketide synthase have been identified, while these synthases catalyse broadly similar reactions they act in very different ways and have significantly different quaternary protein structures.

A wide range of polyketides has been identified from natural sources, and it is believed that only a small fraction of the potential diversity from the natural pool has been sampled to date. There is a clear interest in the discovery of alternative routes to find or generate polyketides of novel structure. The discovery that the biosynthesis of Type I polyketides occurs in an ordered fashion (Cortés et al., Nature (1990) 348, 176-178, Donadio et al., Science (1991) 252, 675-679, Donadio et al., Gene (1992) 111, 51-60, Donadio et al., PNAS (1992) 90, 7119-7123, WO93/13663) and the subsequent experiments that showed that portions of the genes encoding these large multifunctional proteins could be swapped between proteins to produce a 'hybrid PKS' has greatly expanded the potential repertoire of molecules that can be produced by biological routes (U.S. Pat. No. 6,271,255; WO 98/01546). For example, it is possible to replace each of the methylmalonyl-CoA specific acyltransferases of the erythromycin cluster with an AT specific for malonyl-CoA to produce a hybrid PKS-containing strain that can biosynthesise a macrolide polyketide core lacking a methyl group at the expected position (WO 98/01546, Petkovic, H et al, 2003, J Antibiot (Tokyo). 56(6): 543-51). Similarly, it is possible to substitute or alter the reductive loops to leave an altered oxidation state at positions around the ring (WO 98/01546, WO 98/01571, and WO 00/01827). Such techniques involving the genetic engineering of a Type I PKS are applicable to all polyketides synthesised by such Type I enzymes.

In many cases to gain a commercially useful compound the polyketide is used as a template for semi-synthetic derivatisation. In addition to altering/modifying the activity of the molecule such derivatisation might confer a range of properties on the molecule that affects its pharmacological properties, for example but without limitation, altered bioavailability or stability.

One of the important aspects of genetic manipulation of the systems that biosynthesise such molecules is the ability to provide a chemical 'handle' for the addition of such derivative groups, for example replacement of a methylene group by a hydroxyl group by substituting the components of the reductive loop. The ability to feed such a modified polyketide into a combinatorial chemistry program greatly increases the number of altered molecules that are generated and that can be screened for the optimal activity or indeed for entirely different properties/activities. In addition however, the underivatised manipulated molecule may also have desirable properties over the original molecule.

Erythromycin is one of the key members of a class of polyketide molecules containing a 14-membered macrolide ring. Other members of this class include, without limitation, oleandomycin, megalomycin, narbomycin and pikromycin (Shiomi, K & Omura S, 2002, Macrolide Antibiotics: Chemistry, Biology and Practice, Ed. Omura, S, Academic Press, $2^{nd}$ Edition, pp 1-56). Different members of the class of 14-membered macrolides are able to display a range of oxidation states at positions around the ring and a range of substituent groups (for example but without limitation, H—, methyl-, methoxy- or ethyl-) around the ring. 14-membered macrolides can be modified by addition of other groups such as glycosyl groups or other modifications (e.g. methylation, acetylation etc). Other modifications have been introduced chemically (Sunazuka, T et al, 2002, Macrolide Antibiotics: Chemistry, Biology and Practice, Ed. Omura, S, Academic Press, $2^{nd}$ Edition, pp 99-180).

Many of the naturally available chemical handles on the erythromycin molecule have already been used to produce altered erythromycins. For example the 6-hydroxy group has been methylated to produce the commercially available antibiotic clarithromycin. The same position has been modified using a range of other groups to produce compounds such as ABT-773 via the C6-O-allyl intermediate (WO 98/09978; Ma et al., J. Med Chem (2001) 44, 4137-4156). Additionally, it has been reported that the 11- and 12-hydroxy groups have been derivatised (Ku et al., J. Antibiotics (1999) 52, 908-912). The secondary and tertiary hydroxyl groups at C11 and C12 respectively have been used to produce the C11, C12-cyclic carbamate structures seen, for example in telithromycin (Bryskier A., (2000) Clin Microbiol Infect. 6(12): 661-9). The 9-keto group is used to produce the Azithromycin derivatives and has been used to prepare C-9 amino ketolides (Ballow C H & Amsden G W, 1992, Ann Pharmacother.; 26(10): 1253-61; Retsema J and Wenchi F; 2001, International Journal of Antimicrobial Agents, 18, pp S3-S10). Removal of the deoxyhexose moiety at C3 and oxidation of the resulting secondary hydroxy group to a keto group results in the ketolide series. Additionally, the available chemical handles on the sugar moieties have also been modified. Kaneko and co-workers (Kaneko et al., Exp. Opin. Ther. Patents (2000) 10, 1-23) have reviewed some of the recent developments in the area of macrolide antibiotics and describe many other similar modifications around the molecule although this is unlikely to be an exhaustive list of modifications that are possible.

The ability to further increase the number of chemical handles around the molecule would result in novel series of erythromycin compounds by utilization of such handles for semi-synthetic derivatisation. Indeed, many of the chemical methods currently utilising the existing handles may also be used to derivatise new chemical handles, if they could be built into a molecule. Additionally, if it is possible to build into a molecule a chemical handle of a type that does not already exist, then it may be possible to use a different array of chemistries. For example, it will be understood that it would be beneficial to introduce a primary hydroxyl group if a molecule only contained secondary or tertiary hydroxyl groups as this would allow a chemist to specifically derivatise the primary hydroxyl group using chemical methods specific for primary alcohol groups.

A series of compounds of particular interest are those containing alterations in the starter unit area of the molecule (U.S. Pat. No. 6,271,255; WO 98/01546). In the natural erythromycin molecule this starter unit comprises a C13-ethyl group. This is generally considered an unreactive area of the molecule and hence is unavailable for conventional chemical modification, especially in the context of such a molecule that contains many other, more labile, chemical groups. Consequently, a number of novel techniques have been devised to produce alternative polyketide 14-membered macrolide molecules, and particularly erythromycins possessing altered starter units, for example: replacement of the loading module (U.S. Pat. Nos. 6,271,255, 6,437,151, WO 98/01571, Marsden et al., Science (1998) 279, 199-202; Pacey et al., J. Antibiotics (1998) 51, 1029-1034) or N-acetyl cysteamine ester feeding (Jacobsen et al., Science (1997) 277, 367-369). These techniques may require the feeding of precursors to strains that are modified in some way to accept the novel substrates. In some cases the supply of natural substrates is inhibited to allow the acceptance of the novel substrate. However, these techniques are limited as the natural degradative pathways in the cell (e.g. β-oxidation, lipase) compete with the secondary metabolic pathways to reduce the effective amounts of the precursor compounds available and hence the final yield of desired compound in the cell (Frykman et al., Biotechnol. Bioeng. (2001) 76, 303-310). A further disadvantage of these methodologies is that competition of the fed starter with the natural endogenous starter substrates can result in a mixture of products (Pacey et al., J. Antibiotics (1998) 51, 1029-1034).

Other methods that could be used to produce 14-membered macrolides with hydroxylated starters include increasing the numbers of extension cycles that a Type I PKS responsible for the formation of a 14-membered macrolide performs. This can lead to the formation of an octaketide molecule which may cyclise to form a 14-membered macrolide with an extended exocyclic moiety. Methods for producing such molecules are detailed in for example (WO 93/13663, U.S. Pat. No. 6,271,255; WO 98/01546; WO 99/36546; Rowe et al., Chem. Biol. (2001) 8, 475-485). However, Rowe et al., (Chem. Biol. (2001) 8, 475-485), indicate that the introduced extension cycle is sometimes skipped, and that a mixture of molecules including both 14- and 16-membered molecules is produced due to different possible cyclisation patterns that are possible for a linear polyketide molecule catalysed by the polyketide chain termination/cyclisation domain (thioesterase).

Therefore, there is a need to develop alternative methods of generating altered starter units or for activating the starter unit-derived portions of 14-membered macrolides such as erythromycin to provide molecules or templates for molecules with altered antibacterial or other pharmaceutical activity.

One alternative method to activate the starter unit of a polyketide would be to use an enzyme that specifically hydroxylates the starter unit of a polyketide. One potential candidate for this type of enzyme is a cytochrome P450. These enzymes possess a strong oxidizing potential and it is known that some such enzymes are able to act in the later stages of polyketide biosynthesis. Wide ranges of cytochrome P450 hydroxylases have been identified, including many that act specifically in polyketide biosynthetic pathways. It is also known that cytochromes P450 play a significant role in the degradation of drug-like substances in mammalian systems and they act similarly in bacterial cells through catabolic/xenobiotic pathways. They are also known to act on agrochemicals and environmental pollutants. Key to this approach is to develop a system that is efficient and that can act relatively specifically to the starter unit. Other oxidative enzymes such as flavin dependent monooxygenases and non-heme iron dependent dioxygenases exist.

Cytochromes P450 show a high degree of stereo- and regiospecificity, which can have wide industrial application including the production of statins and corticosteroids. Cytochromes P450 have been used for the preparation of valuable drug metabolites and structural studies of human cytochromes P450 are aiding the design of drugs.

A number of cytochromes P450 that act on 14-membered macrolides have been identified and cloned. These have been shown to act on glycosylated or non-glycosylated macrolide substrates depending on the specificity of the enzyme. For example:

EryF—which acts at the C6 position of the erythromycin aglycone 6-dEB (6-deoxy erythronolide B, Andersen, J. F. and C. R. Hutchinson (1992). Journal of Bacteriology 174(3): 725-735).

EryK—which acts at the C12 position of erythromycin D, i.e. after glycosylation at the C3 and C5 hydroxy groups (Stassi, D., S. Donadio, et al. (1993). Journal of Bacteriology 175(1): 182-189).

OleP—which acts to introduce an epoxide group at the C8, C8a position during biosynthesis of oleandomycin (Shah, S., Q. Xue, et al. (2000). Journal of Antibiotics 53(5): 502-508).

PikC hydroxylase—which has a dual specificity, acting at C12 of the 14-membered narbonolide structure and at C10 and C12 of the 12-membered 10-deoxymethynolide structure (Xue, Y. Q., D. Wilson, et al. (1998). Chemistry & Biology 5(11): 661-667). Note that this oxidation results in the hydroxylation of the starter unit region of the 12-membered methynolide but this does not appear to occur on the 14-membered narbonolide Cytochromes P450 acting at various positions on 16-membered macrolide rings such as tylosin are well documented; again said oxidation can occur before or after glycosylation. However, to date although a small number of cytochromes P450 acting on the starter unit region of glycosylated 14-membered macrolides such as erythromycin have been identified, they have not been well described. Additionally, to date no cytochromes P450 which act to hydroxylate the starter unit region of unglycosylated 14-membered macrolides such as erythronolides have been described. Examples of 14-membered macrolide natural products do exist in which the starter unit region appears to be hydroxylated; e.g. CP-63693 (U.S. Pat. No. 4,543,334) and lankamycin. However, it is not known whether such oxidations occur before or after glycosylation, indeed in the lankamycin case this hydroxyl could in principle be polyketide derived (as opposed to introduced after polyketide formation). Recently the entire biosynthetic cluster for lankamycin has been published, revealing the presence of two encoded cytochromes P450 although it is not known at what position each of these act (C8 or C15) and analysis of the PKS shows that 2-methylbutyrate is a likely starter unit (Mochizuki et al., Mol. Microbiol. (2003) 48, 1501-1510).

Recently, the structural determination of the 50S subunit of the ribosome has shown that the nature of their sugar attached has a strong influence on the binding of macrolide antibiotics to the ribosome (Harms et al., Cell (2001) 107, 679-688; Schlunzen et al., Nature (2001) 413, 814-821; Hansen et al., Mol. Cell (2002) 10, 117-128). Therefore, there is a need to develop methods of producing 14-membered macrolides that possess altered glycosylation patterns. It is thought such information on the binding of the macrolides to the ribosome will greatly aid the rational design of macrolide antibiotics that might overcome the typically encountered resistance mechanisms such as methylation or modification of residues/nucleotides within the ribosome. Such studies also demonstrate a significant contribution to binding from the starter unit derived portion of the molecule, hence it is an advantage to be able to alter the nature of the starter unit derived portion and/or the glycosyl groups attached.

The present invention provides a method to combine functional changes at the starter unit region (e.g. hydroxylation at the 14- or 15-position of 14-membered macrolides) with an ability to transfer a range of different glycosyl groups. This method enables the production and isolation of a diverse range of novel macrolide molecules, which may be then optionally be tested for optimal functionality.

In one aspect the present invention provides a method for the generation of hydroxylated 14-membered macrolide compounds, said method comprising producing a 14-membered aglycone template and feeding said 14-membered aglycone template to a strain or range of strains to produce a range of novel compounds that differ in the hydroxylation state of the starter unit region. In one embodiment, the aglycone template is fed to a single strain. In an alternative embodiment, the aglycone template is fed to a range of strains.

In a further aspect, the present invention additionally provides a method for the generation of 14-membered macrolide compounds, said method comprising feeding a hydroxylated aglycone precursor generated as described above, to a strain or range of strains to produce a glycosylated compound or range of compounds containing a range of sugar moieties.

Biotransformation of erythronolide B to produce a compound hydroxylated at the 15-position has been shown previously (Spagnoli et al., J. Antibiotics (1983) 36, 365-375; U.S. Pat. No. 4,429,115). This system used a blocked mutant of *S. antibioticus* (which normally produces the 14-membered macrolide oleandomycin) as the biotransforming organism. A mixture of 4 compounds were produced, 3-O-oleandrosyl-5-O-desosaminyl-15-hydroxyerythronolide B, 3-O-oleandrosyl-5-O-desosaminyl-erythronolide B, 3-O-oleandrosyl-5-O-desosaminyl-(8S) 8-hydroxyerythronolide B and 3-O-oleandrosyl-5-O-desosaminyl-(8R) 8, 19-epoxy-erythronolide B (U.S. Pat. No. 4,429,115). In this case it was determined that the hydroxylation occurred after glycosylation (Spagnoli et al., J. Antibiotics (1983) 36, 365-375). It is noteworthy that hydroxylation was observed at both the C8 and C15 positions of the macrolide ring.

Biotransformation of the 14-membered macrolide 11-acetyllankolide (a 14-membered macrolide aglycone) using a blocked mutant of the erythromycin producing organism *Streptomyces erythreus* (since reclassified as *Saccharopolyspora erythraea*) resulted in production of 15-deoxy-15-oxo 11-acetyllankolide (Goldstein et al., J. Antibiotics (1978) 31, 63-69). In this case oxidation of the starter unit region does occur on an unglycosylated 14-membered aglycone, although the starter unit region is already functionalised with a hydroxy group present at the 15-position; oxidation converts the hydroxy group to a keto group.

14-hydroxyclarithromycin is observed as a metabolite of clarithromycin produced by the action of one of the major cytochromes P450 in the liver. Obviously, in vivo, hydroxylation of clarithromycin must occur after glycosylation. Additionally, methods that have been described for the synthesis of 14-hydroxyclarithromycin and related compounds have involved hydroxylation of the active glycosylated compound (EP 0 222 186, U.S. Pat. No. 4,672,056, Adachi et al., J. Antibiotics (1988) 16, 966-975). In these cases a range of compounds are produced and the route to the compound (feeding erythromycin A to human volunteers and extracting the metabolites from their urine) is unlikely to represent a large-scale production route. As the inventors of EP 0 222 186 acknowledge, this does not occur, for example, using homogenates of rat liver, further reducing the likelihood that it will result in a cost effective route. A route to produce 14-hydroxyclarithromycin from clarithromycin by bioconversion using the fungus *Mucor circinelloides* has been shown (Sasaki et al., J. Antibiotics (1988) 41, 908-915).

In the two previous examples of 14- or 15-hydroxylation of 14-membered macrolides, glycosylation occurred prior to hydroxylation, therefore at no point was the hydroxylated aglycone precursor formed. Additionally, the sequence of events results in a limited ability for a person skilled in the art to select the sugars that are attached in each case. In contrast, the present invention provides for the synthesis of a hydroxylated aglycone template that can then be fed to a wide range of natural or recombinant strains, resulting in the addition of a range of sugars and the generation of a wide range of compounds. The present invention is the first example, to our knowledge, of the generation of erythromycin analogues that possess hydroxylation on the starter unit region via hydroxylation of the aglycone template, which is later glycosylated. Previous studies had assumed that glycosylation occurred first and therefore have not conceived of the present methodology.

The present method has advantages over methods that produce hydroxylated compounds by engineering the polyketide synthase as it does not require the addition of precursors that might be degraded and since the 14-membered macrolide is already formed before hydroxylation it reduces the chance that cyclisation can occur to give a 16-membered ring.

The present invention additionally teaches that once a cytochrome P450 has been identified that is capable of hydroxylating the starter unit region of a 14-membered aglycone it would be possible to clone the gene encoding the cytochrome P450 and express this gene in an alternative host. Thus by expressing such a gene in a host capable of producing the 14-membered aglycone it is possible to produce a strain able to produce the appropriately hydroxylated 14-membered aglycone directly. Similarly it would be possible to engineer a strain that is able to perform both the hydroxylation of the starter unit region and the subsequent glycosylation of the hydroxylated 14-membered aglycone The present invention provides methods for transforming the starter unit region of the aglycone of a 14-membered macrolide biosynthetic pathway by biotransformation and, optionally, subsequent processing of the molecule so produced into a glycosylated form by the addition of one or more sugar moieties; and molecules produced by the methods of the present invention.

The 14-membered macrolide analogues of the present invention also possess further utility as intermediates for the synthesis and semi-synthesis of antibacterial C14- or C15-hydroxyerythromycin or other 14-membered macrolide derivatives.

SUMMARY OF THE INVENTION

The present invention provides methods of transforming the starter unit region of an erythromycin precursor by biotransformation and optionally processing the molecule so produced into a glycosylated form; and compounds produced by said methods.

In one aspect the present invention provides a method for the generation of macrolide compounds, said method comprising feeding a 14-membered macrolide aglycone (the aglycone precursor) to a strain or range of strains to produce one or more compounds that differ from the aglycone precursor in the hydroxylation state of the starter unit region. Therefore, in one aspect the present invention provides a method for generating hydroxylated 14-membered macrolide compounds said method comprising:

(a) producing a 14-membered aglycone template (b) feeding said aglycone template to a strain capable of hydroxylating the aglycone template at the 14 and/or 15 position.

In one embodiment the strain is identified by screening a library of prokaryotes and fungal strains to identify those which are capable of hydroxylating the aglycone template at the 14 and/or 15 position. In an alternative embodiment, the strain is identified by screening a library of actinomycetes. In one embodiment the strain is selected from the group consisting of *Streptomyces eurythermus* DSM 40014, *Streptomyces avermitilis* ATCC® 31272 and *Streptomyces rochei* ATCC® 21250.

In a specific family of embodiments the compounds differ in the hydroxylation state of the 14 or 15 position. In one embodiment the aglycone precursor is as shown by the formula below:

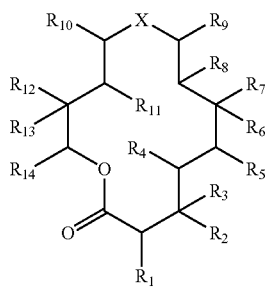

Where:
X=—C(=O)—, —CH(OH)— or —CH$_2$—, $R_1$, $R_4$, $R_6$, $R_9$, $R_{10}$ and $R_{12}$ are each independently H, OH, $CH_3$, $CH_2CH_3$ or $OCH_3$; $R_2$=OH; $R_3$=H; or $R_2$ and $R_3$ together are =O; $R_5$=OH; $R_7$=H, OH or $OCH_3$; $R_8$=H, OH or keto; $R_{11}$=H, OH; $R_{13}$=H, OH, and $R_{14}$=

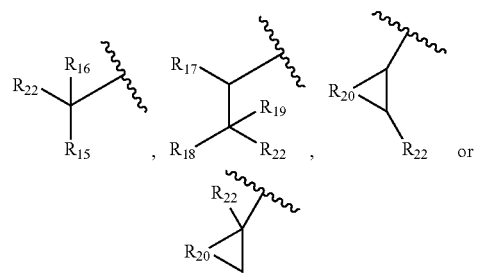

where: $R_{15}$ is H or a $C_1$-$C_7$ alkyl group or $C_4$-$C_7$ cycloalkyl group; $R_{16}$ is H, a $C_1$-$C_7$ alkyl group or $C_4$-$C_7$ cycloalkyl group, $R_{17}$, $R_{18}$ and $R_{19}$ are each independently H or a $C_1$-$C_7$ alkyl group or $R_{20}$ or $R_{21}$ are $(CH_2)_x$ where x=2-5 and $R_{22}$ is H; or a compound as defined above modified by replacing one or more >CHOH or >CHOR groups by a keto group, or a compound as defined above which differs in the oxidation state of one or more of the ketide units (i.e. selection of alternatives from the group: —CO—, —CH(OH)—, alkene —CH—(=CH— or —CH=), and $CH_2$). Generally, this and similar formulae encompass all stereochemical forms, unless the context requires otherwise. In particular, the stereochemistry of any —CH(OH)— is generally independently selectable.

In a preferred embodiment, X=—C(=O)—, $R_1$=$R_4$=$R_6$=$R_9$=$R_{10}$=$R_{12}$=$CH_3$, $R_2$=OH, $R_7$=H, OH; $R_8$=H, OH, $OCH_3$; $R_{11}$=H, OH; $R_{13}$=H, OH; $R_{14}$=

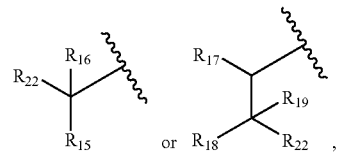

where: $R_{15}$=H, $CH_3$, or $CH_2CH_3$ and $R_{16}$ is H; or $R_{17}$ and $R_{18}$ are each independently H or $CH_3$; $R_{19}$ and $R_{22}$ are H.

In a more highly preferred embodiment the aglycone precursor is erythronolide B and the compounds produced are 14-hydroxy and/or 15-hydroxyerythronolide B. In another preferred embodiment of the invention, the aglycone precursor is 6-deoxyerythronolide B (6-dEB) and the compounds so produced are 14-hydroxy 6-dEB and/or 15-hydroxy 6-dEB. In another preferred embodiment of the invention the aglycone precursor is derived from a PKS engineered by the methods described in WO 98/01546, and it undergoes hydroxylation at the C14 and/or C15 positions. In a preferred embodiment the PKS is engineered to incorporate an alternative starter unit that can be subsequently hydroxylated. In a further preferred embodiment the aglycone precursor formed by the engineered PKS differs at some other point of the molecule, for example by incorporation of a malonyl-CoA moiety instead of methylmalonyl-CoA at one of the extension cycles or alternatively displays a different oxidation state to that typically found on the erythronolide (or other macrolide produced by the un-engineered PKS) or alternatively a combination of such changes.

In one type of embodiment the strain is a wild-type strain that naturally contains the ability to hydroxylate the aglycone at the starter unit region. In an alternative type of embodiment a strain is genetically engineered to express a cytochrome P450 capable of hydroxylating the starter unit region of the aglycone template provided. In particular, the gene encoding a cytochrome P450 that is inserted into the strain may be identified by cloning the cytochrome P450 gene(s) from the strains identified as described herein as being capable of hydroxylating the starter unit region of a 14-membered macrolide. Therefore, as an example of how this may be done, we describe the identification of a cytochrome P450 from the lankamycin cluster in *S. rochei*. We have shown that this cytochrome P450 is apparently able to hydroxylate the propionate starter unit of erythronolide B in addition to the 2-methyl-butyrate starter unit that is apparently incorporated by the lankamycin PKS (Mochizuki et al., Mol. Microbiol. (2003) 48, 1501-1510).

In one embodiment, the strain used in step (b) is a prokaryote or a fungal strain. In a preferred embodiment the strain is *E. coli*. In a more preferred embodiment the strain is an actinomycete. In an alternative preferred embodiment the strain is selected from the group consisting of: *Saccharopolyspora erythraea, Streptomyces coelicolor, Streptomyces avermitilis, Streptomyces griseofuscus, Streptomyces cinnamonensis, Streptomyces fradiae, Streptomyces eurythermus, Streptomyces longisporoflavus, Streptomyces hygroscopicus, Saccharopolyspora spinosa, Micromonospora griseorubida, Streptomyces lasaliensis, Streptomyces venezuelae, Streptomyces antibioticus, Streptomyces lividans, Streptomyces rimosus, Streptomyces albus, Amycolatopsis mediterranei, Nocardia sp, Streptomyces tsukubaensis* and *Actinoplanes* sp. N902-109.

In an alternative embodiment, the method of the present invention additionally comprises the step of (c) feeding the resulting hydroxylated aglycone to a second strain which is able to add one or more sugar moieties.

In one embodiment the cytochrome P450 is cloned into a strain that produces the 14-membered aglycone, thus allowing production of the hydroxylated 14-membered aglycone in a single strain.

In an alternative embodiment of the present invention the hydroxylated aglycone product is isolated after step (b). In an alternative embodiment, said hydroxylated aglycone produced is fed directly to the strain of step (c) with no purification step.

In an additional aspect the present invention provides a method for the generation of macrolide compounds, said method comprising feeding a starter unit region-hydroxylated 14-membered aglycone precursor generated as described above, to a strain or range of strains to produce a glycosylated compound or range of compounds containing a range of sugar moieties. Therefore, the present invention provides a method to combine functional changes in the starter unit region with an ability to transfer a range of different glycosyl groups. This method enables the production and isolation of a diverse range of macrolide molecules.

In a specific aspect, the present invention provides a method for the generation of 14-hydroxyerythronolide B, and optionally its glycosylation by the natural sugars or alternative or modified sugars. In one embodiment the method of the present invention includes introducing into said strain gene cassette(s) containing the biosynthetic genes responsible for the synthesis of the desired sugar(s).

In a specific aspect, the present invention provides a method for the generation of 15-hydroxyerythronolide B, and optionally its glycosylation by the natural sugars or alternative or modified sugars.

In a specific aspect, the present invention provides a method for the generation of 14-hydroxy 6-deoxy erythronolide B, and optionally its glycosylation by the natural sugars or alternative or modified sugars.

In a specific aspect, the present invention provides a method for the generation of 15-hydroxy 6-deoxy erythronolide B, and optionally its glycosylation by the natural sugars or alternative or modified sugars.

In one embodiment, glycosylation of the 14-hydroxy or 15-hydroxy aglycones results in the transfer onto the C3 and C5 positions of the natural sugars (e.g. in the erythromycin series, at C3 mycarose which is subsequently methylated to form cladinose and at C5 desosamine). In an alternative embodiment non-natural sugars (i.e. sugars not naturally found on the erythromycin molecule, for example but without limitation, rhamnose and methylated derivatives thereof (2'-O methyl, 2',3'-bis or 2',3',4'-tris-O-methyl), digitoxose, olivose, oliose, oleandrose, mycaminose or angolosamine) are transferred to the C3 or C5 position. In a further embodiment non-natural sugars are added to the C3 position but the C5 sugar remains natural. In a further embodiment the C5 sugar is non-natural whereas the C3 sugar is natural. In yet a further embodiment the hydroxylated aglycone template is glycosylated at alternative sites, i.e. not only C3 and/or C5. In a further embodiment one or more additional glycosyl group(s) are transferred on to an existing glycosyl group to form a disaccharide.

In another aspect, the present invention provides for the use of the 14-membered hydroxylated aglycones, including, without limitation 14- or 15-hydroxyerythrolide B, as intermediates for the synthesis of $C_{1-4}$-hydroxylated or $C_{1-5}$-hydroxylated erythromycins or 14-membered macrolide derivatives. In particular, the isolation of compounds according to formula I below is specifically contemplated by the present invention.

In a further aspect, the present invention contemplates the generation of novel 14-membered macrolide derivatives via semi-synthetic modification of compounds according to formula I.

Definitions:

As used herein, the term "14-membered macrolide" includes naturally occurring erythronolides and analogues thereof e.g. those described in U.S. Pat. No. 6,271,255 and WO 98/01546, naturally occurring erythromycins, pikromycins, oleandomycins, megalomycins, narbomycins and analogues thereof. The term macrolide encompasses both the glycosylated end product and the non-glycosylated aglycone.

As used herein, the term "14-membered aglycone" refers specifically to 14-membered macrolides as described above which have no glycosyl groups attached.

As used herein, the term "hydroxylated aglycone" refers to an aglycone that differs from the naturally occurring template in the hydroxylation state of the starter unit region (i.e. position C14 or 15- for the 14 membered aglycone templates).

As used herein the term "starter unit" refers to the group attached to the C13 position in the 14-membered macrolide. In the natural erythromycin molecule this is an ethyl group (comprising carbons 14 and 15); this is derived from propionyl CoA with the third carbon thereof being carbon 13.

DETAILED DESCRIPTION OF THE INVENTION

In the present invention a library of organisms were screened to identify organisms that were capable of hydroxylating 14-membered macrolide aglycones that are the precursors to compounds such as erythromycin. Specifically, strains were screened for their ability to hydroxylate the aglycone precursor of erythromycin, namely erythronolide B. One strain identified using this method was *Streptomyces eurythermus* DSM 40014. Subsequent isolation and structural characterization of the compounds produced by MS and NMR methods demonstrated that this hydroxylation occurs on the 14- or the 15 positions of the molecule to produce a mixture of 14- and 15-hydroxy EB.

Therefore, in one aspect the present invention provides a method for the hydroxylation of the starter unit region of 14-membered aglycones in vivo by biotransformation, said method comprising feeding said aglycone to a strain and optionally isolating the compounds produced. In a specific embodiment, the hydroxylation occurs at either position 14- or at position 15- on the 14-membered macrolide. In a preferred embodiment the aglycone is erythronolide B.

*S. eurythermus* was found to bioconvert erythronolide B to both 14- and 15-hydroxy EB allowing the production of both the 14- and 15-hydroxyerythromycin series; therefore in a specific embodiment the method comprises feeding the aglycone to *S. eurythermus*.

Although *S. eurythermus* is capable of producing 14-hydroxy and 15-hydroxyerythronolides, in some instances it is preferable to have a strain that produces a single compound. This may have downstream processing advantages or cost benefits in reducing the numbers of purification steps required to isolate the single desired component from the undesired component(s) or to separate desired compounds. To identify such a strain, a library of actinomycete organisms was further screened to find strains that could convert 14-membered aglycone precursors, in particular EB to a single population of hydroxyerythronolide. A range of media was used to optimise conditions. Two strains, *Streptomyces avermitilis* ATCC 31272 and *Streptomyces* rochei ATCC 21250 were identified that produced the 15-hydroxy EB but did not produce 14-hydroxy EB at significant levels.

Therefore, in an additional aspect, the present invention provides a method for the production of 15-hydroxy EB comprising feeding EB to *S. avermitilis* ATCC 31272 or to *S. rochei*ATCC 21250 and optionally isolating the compound produced.

A person skilled in the art will appreciate that a similar round of screening of a library of organisms can be used to identify a strain that specifically produces 14-hydroxy EB. Additionally, it is clear to someone of skill in the art that using the methods described herein alternative strains capable of converting EB to 14- and 15-hydroxy erythronolides can be identified; these strains are also within the scope of the present invention. Such strains could be prokaryotic or eukaryotic including fungal strains.

In an alternative aspect, a strain capable of generating hydroxylated aglycones can be generated by expressing in a suitable host cell, DNA encoding a cytochrome P450 that acts to hydroxylate the starter unit region of the 14-membered aglycone precursor. In this context a preferred host cell strain is a mammalian cell strain, fungal cells strain or a prokaryote. More preferably the host cell strain is *Pseudomonas*, mxyobacteria or *E. coli*. In a still more preferred embodiment the host cell strain is an actinomycete, still more preferably including, but not limited to *Saccharopolyspora erythraea, Streptomyces coelicolor, Streptomyces avermitilis, Streptomyces griseofuscus, Streptomyces cinnamonensis, Streptomyces fradiae, Streptomyces eurythermus, Streptomyces longisporoflavus, Streptomyces hygroscopicus, Saccharopolyspora spinosa, Micromonospora griseorubida, Streptomyces lasaliensis, Streptomyces venezuelae, Streptomyces antibioticus, Streptomyces lividans, Streptomyces rimosus,* *Streptomyces albus, Amycolatopsis mediterranei, Nocardia* sp, *Streptomyces tsukubaensis* and *Actinoplanes* sp. N902-109.

An alternative series of preferred host cells are eukaryote, a particularly preferred host is a mammalian, plant, yeast or fungal cell. A still more preferred eukaryotic cell is a fungal strain, more preferably strains such as *Aspergillus terreus* and *Aspergillus nidulans*.

In an alternative aspect the cytochrome P450 is cloned into a strain that produces the 14-membered aglycone, thus allowing production of the hydroxy 14-membered aglycone in a single strain.

In a still further aspect the cytochrome P450 known to hydroxylate the aglycone is cloned into a strain that produces a 14-membered glycosylated macrolide with a non-hydroxylated starter unit region. This enables the hydroxylation to occur prior to the glycosylation step. It is possible to transfer one or more sugars after hydroxylation. Since in many cases the aglycone and hydroxy aglycone are recognised equally by the various glycosyltransferases it may be beneficial to control the timing of the starter hydroxylation, and/or the glycosylation, to ensure that maximal hydroxylation can occur before the glycosyl groups are transferred.

In an alternative aspect the cytochrome P450 could be isolated from the cell and used to hydroxylate the substrate in vitro. Alternatively the protein could be attached to a solid support and used to hydroxylate the substrate.

In a further aspect of the invention we specifically contemplate using these strains to hydroxylate the related erythronolide 6-deoxyerythronolide B (6-dEB). This compound has the same structure as EB but lacks the C6-hydroxyl group that is attached by the action of EryF. After feeding this compound to *S. rochei* or *S. avermitilis* grown under similar conditions to those fed EB a more polar peak with m/z consistent with the presence of 15-hydroxy 6-dEB would be identified, a person skilled in the art could identify and isolate the desired compound from the range of products formed using standard techniques. This demonstrates that hydroxylation of the starter unit region is not dependent on the presence of the C6 hydroxy group and indicates that the techniques described herein are also applicable to the a range of 6-dEBs including those which have been produced via PKS engineering and/or those which have incorporated alternative starter units. Feeding the 6-dEB compound to the *S. eurythernus* strain described earlier would likely produce both the 14- and 15-hydroxy-6-dEB species.

In a still further aspect of the invention recombinant aglycones with starter units differing from that usually found on EB are fed to strains capable of hydroxylating at C14 or C15 to demonstrate hydroxylation at the starter unit region.

In a further aspect of the invention aglycones altered in the aglycone ring portion of the molecule (e.g. lacking a methyl group or displaying altered oxidation state at some point around the ring) are fed to strains capable of hydroxylation of the C14 or C15 position to demonstrate hydroxylation of the starter unit region.

The present invention further contemplates the generation of glycosylated derivatives of the hydroxylated aglycones generated using the methods described above. In one embodiment, the hydroxylated aglycone is fed to *S. erythraea* which results in the production of the glycosylated compounds. In a specific embodiment the aglycone template is EB and the resulting 14-hydroxy EB and 15-hydroxy EB are fed to *S. erythraea* to generate the respective 14-hydroxy and 15-hydroxyerythromycins.

In a further embodiment, a *S. erythraea* mutant blocked in the ability to produce the aglycone is used to biotransform the hydroxylated aglycone templates to the glycosylated 14-membered macrolide erythromycins. *S. erythraea* JC2, (Rowe et al., Gene (1998) 216, 215-223) is a derivative of the *S. erythraea* NRRL2338 strain from which the entire PKS region, apart from a small fragment which encodes part of the terminating TE domain, has been specifically deleted. This strain can be used to biotransform the 14- and 15-hydroxy EB to their respective erythromycins as it retains the ability to glycosylate and hydroxylate erythronolide macrolactones.

It will be understood by those skilled in the art that alternative strains can be constructed or produced, in which the ability of the *Sacch. erythraea* strain to produce the aglycone is impaired while still retaining the downstream processing activities, for example but without limitation glycosylation, that result in the conversion of the aglycone template to the respective erythromycin. Such strains might include for example KS1 knockout strains in which the active site cysteine of the PKS KS1 has been mutated to a non-functional amino acid residue, for example alanine. UV mutagenesis could be used to cause mutations in the PKS, screening for erythromycin non-producers by biological screen, followed by a screen to distinguish those strains possessing mutations in regions of the chromosome that contribute to the synthesis of the aglycone, all such strains are within the scope of the present invention. Glycosylation can alternatively be achieved by feeding the hydroxylated aglycone to a strain that is not impaired in the ability to produce the aglycone (i.e. a wild type Sacch. erythraea) but this results in a mixture of products.

In one embodiment of the invention, the hydroxylated aglycones are first isolated before feeding to the second strain. This has advantages in that it is likely to be easier to separate and purify the hydroxylated erythronolides or hydroxylated 14-membered aglycones than to separate their respective hydroxy-14-membered glycosylated macrolides, especially if the strain chosen for the hydroxylation is able to hydroxylate at either the 14- or 15-positions. However, it is obvious to a person of skill in the art that an alternative process could be envisaged in which the hydroxy aglycones are not purified or are only semi-purified prior to the glycosylation step in order to speed up the biotransformation process.

It is obvious to one skilled in the art that the C14 or C15 hydroxylated aglycones could be chemically derivatised prior to further biotransformation. Such derivatisation could include but is not limited to alkylation, acylation or glycosylation. Examples of such modification could involve but are not limited to the formation of 14- or 15-methoxy EB or 14- or 15-acetoxy EB, prior to further biotransformation. Alternatively the 14- or 15-hydroxy groups could be modified by displacement reactions including but not limited to the exchange of the hydroxyl groups for halogen atoms such as F, Cl, Br or I, or exchange with a substituted amine. In a similar manner the stereochemistry of the 14-hydroxy group could be inverted, for example, by the use of a Mitsunobu inversion reaction. It is further obvious to one skilled in the art that the 14- or 15-hydroxy groups could be modified by oxidation to provide 14-ketoerythronolides or 15-formylerythronolides or 15-carboxyerythronolides. Furthermore, it is also obvious in the art that the resulting erythronolides with oxidised functionality at C14 or C15 could be protected by formation of, for example, acetal, thioacetal, ketal, ester or amide groups. Methods of selectively derivatising, displacing, oxidising and protecting primary alcohols are well known to those skilled in the art.

The person skilled in the art will appreciate that similar methods of derivatisation may be applied to the glycosylated macrolides, e.g. to produce semi-synthetic derivatives of 14- or 15-hydroxylated 14-membered macrolides.

In a further aspect of the present invention, further diversity from this system is generated by altering the nature of either the glycosyl groups added to the macrolide and/or altering other post-PKS processing steps.

For example, an additional mutation could be made in the JC2 strain to delete the activity of the sugar methyl transferase EryG which acts on the mycarose sugar after glycosylation. Feeding this strain 15-hydroxy EB would produce 15-hydroxyerythromycin C, which contains a mycarose sugar instead of the cladinose generally found on erythromycin A. It would be understood by those skilled in the art that a similar mutation in EryK, the cytochrome P450 hydroxylase that acts at the C12 position would cause production of only 15-hydroxyerythromycin B.

Our experiments showed that the ability of EryK to hydroxylate the C12 position was possibly inhibited by the presence of a hydroxyl group on the starter unit region. The nature of the starter group, and particularly the size of the group, has been shown to influence the proportion of the A-forms produced by these systems (Pacey et al., J. Antibiotics (1998) 51, 1029-1034). A number of methods have been used to increase the production of the desired forms, for example alteration of fermentation conditions. Indeed our experiments showed that when strains were moved from shake flask conditions into fermenters greater proportions of the A-forms could be produced, presumably reflecting the better control of oxygenation that can be achieved in such vessels. Alternatively, it is possible to place the EryK cytochrome P450 under the control of the actI/actII-orf4 promoter-activator systems and overexpress this gene in the glycosylating host. This has been done by upregulating the gene directly (replacing its own promoter) or could alternatively be done by placing an additional copy of this gene at a neutral position in the chromosome; alternative promoters, such as the promoter for resistance to pristinamycin or the ermE* promoter could also be used.

The present invention also demonstrates that it would be possible to produce 14- or 15-hydroxylated, 14-membered macrolides bearing only a single sugar at the C3 position. For example, hydroxylated erythronolides could be fed to a S. erythraea JC2 strain bearing an additional mutation in the desosamine pathway. This would abolish the ability of this strain to produce desosamine, the deoxyamino sugar usually transferred to the C5 position of 3-O-mycarosyl EB. On feeding 14- and 15-hydroxy EB to these strains we would expect to detect production of both the 14- and 15-hydroxy-3-O mycarosyl EB compounds, demonstrating the production of compounds with hydroxylation on the starter unit region but which bear only a single sugar.

It will be apparent to those skilled in the art that other mutations in the desosamine pathway combined with a mutation in the PKS could be used to produce a similar result. Example 10 deletes the activity of EryCIII (the glycosyl transferase that transfers desosamine) in JC2 to achieve the same result. Such compounds bearing a single sugar could also be used as precursor compounds and fed to a strain capable of adding a second sugar. For example, feeding such compounds to the strain JC2 described previously would produce 14- or 15-hydroxyerythromycins.

Additionally, one of skill in the art would appreciate that mutations can be made to the mycarose pathway, which would result in the production of hydroxylated erythromycin analogues that have the desosamine moiety but do not have the sugar attached at C-3 when fed with hydroxyl aglycones. However, additionally, it will be understood by those skilled in the art that production of such compounds relies on the selection of a glycosyltransferase that can readily attach desosamine to an erythronolide. For example, DesVII is known to transfer desosamine to a range of 6-dEB analogues (Tang and McDaniel, Chem. Biol. (2001) 8, 547-555), and would be likely to transfer desosamine to 6-dEBs hydroxylated in the starter region. These authors acknowledged that bioconversion levels in this case were low, however it would be understood by one skilled in the art that these could be improved by further testing this glycosyltransferase (or mutants thereof) or a range of other glycosyl transferases either natural or engineered to better accept substrates modified at various positions round the ring, including ones possessing the C6-hydroxy group.

Alternatively, 14- or 15-hydroxylated aglycones could be fed to S. erythraea strains engineered to produce and transfer other amino sugars, for example, mycaminose or anglosamine to the C5 position. This could be alone or in addition to a sugar attached elsewhere on the ring (i.e. the strain could first transfer mycarose to C3 followed by the attachment of mycaminose to C5).

It will be apparent to one of skill in the art that a similar process can be performed to produce compounds such as 14-hydroxy 3-O-mycarosyl EB and 14-hydroxy 5-O-mycaminosylerythromycins and these processes are considered within the scope of the present invention.

A further set of compounds bearing a single sugar could be produced by feeding 14- or 15-hydroxy EB to a range of strains bearing gene cassettes that confer the ability to biosynthesise a range of neutral sugars. Such experiments are related to those described in WO 03/048375 which describes the feeding of EB to such strains. For example (example 10), by feeding 15-hydroxy EB to a strain *Sacch. erythraea* SGT2 pSGOLEG2 (Gaisser et al., Mol. Microbiol. (2000) 36, 391-401) we demonstrate the production of 15-hydroxy-3-O-rhamnosyl EB. Transfer of the sugar to the C3 position catalysed by EryBV does not appear to be affected by the alteration at the 14/15 position. Similarly, such compounds could be further biotransformed for example by adding desosamine to produce the 15-hydroxy 3-O-rhamnosylerythromycin series. Such processes are applicable to the 14-hydroxy EB series. A wide range of similar sugars could also be introduced at the C3 position e.g. cladinose, rhamnose and methylated derivatives thereof (2'-O methyl, 2',3'-bis or 2',3',4'-tris-O-methyl), digitoxose, olivose, oliose, oleandrose or rhodinose. This method can be applied by a person of skill in the art to construct strains that transfer two alternative sugars to 14- or 15-hydroxy EB and to construct strains that transfer non-neutral sugars to the C5 position of 14 and 15-hydroxy EB.

It is known to those skilled in the art that other glycosylation patterns are shown on 14-membered macrolides. For example but without limitation, megalomycin is a 14-membered macrolide, similar to erythromycin but bearing an additional glycosyl group at the C6 position. Therefore, in a further aspect the present invention provides a method for the generation of 14- and 15-hydroxylated 14-membered macrolides which have been glycosylated at a range of different sites around the aglycone, by introducing the glycosyltransferase capable of acting at a different point of the molecule and associated sugar pathway (or part of if not all is necessary) into a host strain and feeding the 14- or 15-hydroxy aglycone. It would be understood by one skilled in the art that this would require a suitable hydroxyl group at the desired point on the molecule.

In an additional aspect of the invention, 14- or 15-hydroxy-erythronolides can be fed to other wild type strains capable of glycosylating 14-membered macrolides. These strains could, for example, contain a desired deoxysugar pathway and additionally possess a glycosyltransferase able to transfer this sugar to the hydroxylated aglycone. Alternatively these strains could be engineered to express suitable glycosyl transferase(s) and take advantage of the host deoxysugar pathways. The strains could glycosylate the hydroxylated aglycones while at the same time producing the natural products produced by the strain or could be mutagenised or modified in other ways to suppress production of such native compounds. Alternatively the host could be a neutral biotransformation host and either the sugar pathway (or part of) and/or the glycosyltransferase(s) could be introduced into the host as above. It may be necessary to ensure that the desired pathways are expressed under the conditions in which the strains are fed the hydroxylated aglycones.

As discussed above, the 14- and 15-hydroxylated 14-membered aglycones can be readily purified from each other by standard chemical isolation methods prior to the second biotransformation step. However, in some cases it may not be necessary to completely purify the extracts prior to the second step, a simple crude extract followed by biotransformation may be sufficient to allow processing of the aglycone to the corresponding erythromycin compound. In some cases it may be possible to simply transfer the media containing the hydroxylated aglycone into the second biotransformation or alternatively inoculate the media with the second biotransformation strain or alternatively to conduct a co-fermentation experiment with the strain that conducts the C14- and/or C15-hydroxylation and a second strain that adds the desired glycosyl and other groups.

A particular advantage of the two-step biotransformation process described above is that it is possible to alter the post PKS processing of the 14- or 15-hydroxy EB by utilising altered biotransformation hosts. These can either be strains engineered to produce different sugars, strains engineered to be blocked in one of the steps of the biosynthesis of a sugar, strains blocked in one of the steps of the biosynthesis of a sugar resulting in the incorporation of a different sugar or could be strains known to possess alternative sugar pathways and glycosyltransferase able to attach such sugars to 14-membered aglycones. Alternatively, these strains can be engineered to express a glycosyltransferase with such activity.

Therefore, by using the two stage methodology as described above, i.e. production of hydroxylated erythronolides followed by a biotransformation step to add the desired sugar(s) and other groups it is possible to produce a range of 14- or 15-hydroxy 14-membered macrolides bearing different glycosyl groups.

However, although the method described above indicates that each feeding may be a distinct step in the method a person skilled in the art would appreciate that in some cases it may be advantageous to perform a co-fermentation of the two strains. In particular this would allow a reduction in the overall fermentation time required. Therefore, in a further aspect the present invention provides a method for the biosynthesis of 14- and 15-hydroxy 14-membered glycosylated macrolides, said method comprising feeding an aglycone template to a co-fermentation of 2 strains, the first strain being selected from the group consisting of *S. eurythermus, S. rochei* and *S. avermitilis* or other strain capable of hydroxylating the starter unit region of a 14-membered aglycone and a second strain capable of glycosylating the in situ generated hydroxyl aglycone template, and optionally isolating the compounds produced.

Using the methods of the present invention, it is possible to extend the range of molecules produced by this approach by utilizing aglycones derived from recombinant strains. For example, a strain capable of synthesizing erythronolides in which the ethyl substituent at C13 is altered to either isopropyl or secbutyl by transforming an EB producer with a construct designed to replace the natural erythromycin PKS loading module with a loading module derived from the avermectin PKS, known to incorporate branched chain carboxylic acids as starter units (Marsden et al., Science (1998) 279, 199-202; U.S. Pat. No. 6,271,255; WO 98/01546). The erythronolide products from this strain could be fed to *S. eurythermus* to demonstrate that they can also be hydroxylated on the starter unit region by this procedure. Unnatural starter unit erythronolide B analogs can be produced by feeding, for example, cyclobutane carboxylic acid analogs to the strain containing the avermectin loading module. Feeding these novel aglycones to strains such as *S. eurythermus* or *S. rochei* or an alternative strain capable of hydroxylating a 14-membered macrolide starter unit region would result in a starter unit region hydroxylated 14-membered aglycone.

Similarly recombinant techniques can be used to produce 14-membered aglycones that differ at positions around the ring. Feeding these compounds to a strain capable of hydroxylating the starter unit region of a 14-membered aglycone would result in the formation of the corresponding hydroxylated 14-membered aglycone.

In another specific aspect of the present invention, different forms of the 14-membered macrolides can be generated by feeding alternative versions of the aglycone templates. For example; the A-forms of the 14- and 15-hydroxyerythromycins could be generated by feeding erythronolide A produced chemically by degradation of erythromycin. Biotransformation of this compound using the *S. eurythermus* strain under the same conditions used for the production of 14- and 15-hydroxy EB from EB would result in the production of 14- and 15-hydroxyerythronolide A. This compound could be further biotransformed to attach the glycosyl groups desosamine and cladinose (via mycarose) using the strain JC2, which is blocked in the ability to produce the aglycone resulting in the production of the compounds 14-hydroxyerythromycin A and 15-hydroxy erythromycin A. Alternatively, a different range of glycosyl groups could be attached to the hydroxylated erythronolide A aglycones. It will be understood by those skilled in the art that it would be possible to take many naturally occurring 14-membered macrolides that do not contain an activated starter unit region (i.e. lacking a hydroxy or keto group attached to the starter unit region), particularly those containing neutral sugars and hydrolyse the glycosyl groups from the molecule to release the aglycone which can be hydroxylated on the starter unit region by the methods described herein. The resulting hydroxylated aglycones can be glycosylated as desired.

It will be understood by those skilled in the art that it would be possible to further screen a library of actinomycetes as we have done and screen for strains capable of hydroxylating/oxidising the unactivated starter unit region of a 14-membered aglycone in other ways. For example, it is well known that the action of a cytochrome P450 can result in the production of an epoxide group, or similarly to produce a vicinal dihydroxy functionality. Similarly the action of a single cytochrome P450 could result in the oxidation of an unactivated starter unit region directly to the keto functionality. In a similar way an alternative cytochrome P450 could act to convert an unactivated terminal methyl group to a aldehyde moiety or to a carboxylic acid. Furthermore, in some cases oxidation to produce hydroxylated aglycones may be followed by further oxidation to produce the keto or aldehyde functionality (depending on the exact chemical context).

In one aspect, the present invention provides methods for the synthesis of the following compounds according to formula I:

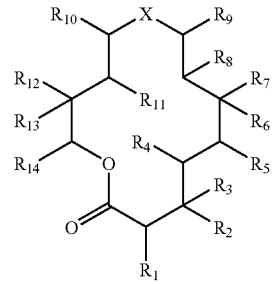

Where:
X=—C(=O)—, —CH(OH)— or —CH$_2$—, R$_1$, R$_4$, R$_5$, R$_{10}$ and R$_{12}$ are each independently H, OH, CH$_3$, CH$_2$CH$_3$ or OCH$_3$; R$_2$=OH, or any glycosyl or disaccharide group, preferably selected from O-cladinose, O-mycarose, O-rhamnose and methylated derivatives thereof (2'-O methyl, 2',3'-bis or 2',3',4'-tris-O-methyl), O-digitoxose, O-olivose, O-oliose or O-oleandrose; R$_3$=H; or R$_2$ and R$_3$ together are keto; R$_5$=OH, or any glycosyl group, preferably selected from O-desosamine, O-mycaminose, O-angolosamine; R$_7$=H, OH, OCH$_3$; R$_8$=H, OH or keto; R$_9$=H, OH, CH$_3$, CH$_2$CH$_3$ or OCH$_3$, O-megosamine, O-cladinose, O-mycarose, O-rhamnose and methylated derivatives thereof (2'-O methyl, 2',3'-bis or 2',3',4'-tris-O-methyl), O-digitoxose, O-olivose, O-oliose or O-oleandrose; O-desosamine, O-mycaminose or O-angolosamine; R$_{11}$=H, OH; R$_{13}$=H, OH, and R$_{14}$

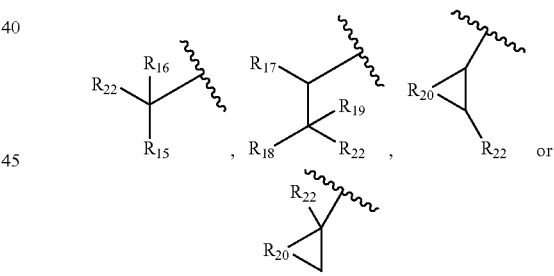

where: R$_{15}$ is H or a C$_1$-C$_7$ alkyl group or C$_4$-C$_7$ cycloalkyl group; R$_{16}$ is H, a C$_1$-C$_7$ alkyl group or C$_4$-C$_7$ cycloalkyl group, R$_{17}$, R$_{18}$ and R$_{19}$ are each independently H or a C$_1$-C$_7$ alkyl group or R$_{20}$ or R$_{21}$, are (CH$_2$)$_x$ where x=2-5 and R$_{22}$ is O—R$_{23}$ where R$_{23}$=H or a C$_1$ to C$_7$ alkyl group or C$_1$-C$_7$ acyl group; or R$_{22}$ and R$_{16}$ together are a keto group; or R$_{22}$ and R$_{19}$ together are a keto group; or a compound as defined above which differs in the oxidation state of one or more of the ketide units (i.e. selection of alternatives from the group: —CO—, —CH(OH)—, alkene —CH— (=CH— or —CH=), and CH$_2$) where the stereochemistry of any —CH(OH)— is also independently selectable.

In a preferred embodiment, the present invention provides the following novel compounds according to formula I:

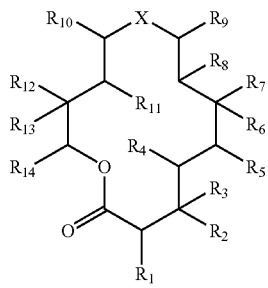

Where:

X=—C(=O)—, —CH(OH)— or —CH$_2$—, $R_1$, $R_4$, $R_6$, $R_9$, $R_{10}$ and $R_{12}$ are each independently H, CH$_3$ or CH$_2$CH$_3$, $R_2$=OH or any glycosyl group, preferably selected from O-cladinose, O-mycarose, O-rhamnose and methylated derivatives thereof (2'-O methyl, 2',3'-bis or 2',3',4'-tris-O-methyl), O-digitoxose, O-olivose, O-oliose or O-oleandrose; $R_3$=H, or $R_2$ and $R_3$ together are keto; $R_5$=OH or any glycosyl group, preferably selected from O-desosamine, O-mycaminose, O-angolosamine; $R_7$=H, OH, OCH$_3$; $R_8$=H, OH, $R_{11}$=H, OH, $R_{13}$=H, OH, $R_{14}$=

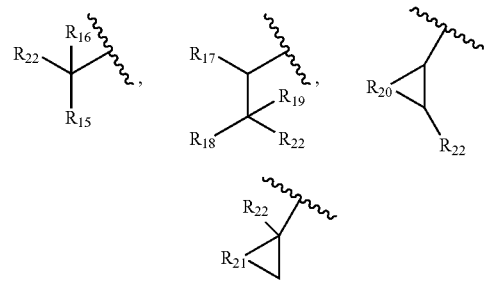

where: $R_{15}$ is H or a C$_1$-C$_7$ alkyl group or C$_4$-C$_7$ cycloalkyl group; $R_{16}$ is H, a C$_1$-C$_7$ alkyl group or C$_4$-C$_7$ cycloalkyl group, $R_{17}$, $R_{18}$ and $R_{19}$ are each independently H or a C$_1$-C$_7$ alkyl group or $R_{20}$ or $R_{21}$ are (CH$_2$)$_x$ where x=2-5 and $R_{22}$ is O—$R_{23}$ where $R_{23}$=H or a C$_1$ to C$_7$ alkyl group or C$_1$-C$_7$ acyl group; or $R_{22}$=halogen or NR$_{24}$R$_{25}$, where $R_{24}$ and $R_{25}$ are each independently H, a C$_1$ to C$_7$ alkyl group or C$_1$-C$_7$ acyl group; or $R_{22}$ and $R_{16}$ together are a keto group; or $R_{22}$ and $R_{19}$ together are a keto group, in a preferred embodiment $R_{22}$ is OH, or a compound as defined above which differs in the oxidation state of one or more of the ketide units (i.e. selection of alternatives from the group: —CO—, —CH(OH)—, alkene —CH—, and CH$_2$) where the stereochemistry of any —CH(OH)— is also independently selectable; with the proviso that the following compounds are excluded:

(a) when $R_2$=OH, O-cladinose or O-mycarose and $R_5$ is OH or O-desosamine (b) when $R_1$=$R_4$=$R_6$=$R_9$=$R_{10}$=$R_{12}$=CH$_3$, $R_3$=H, $R_2$=O-oleandrose, $R_5$=O-desosamine, $R_7$=OH, $R_8$=$R_{13}$=H and $R_{14}$=

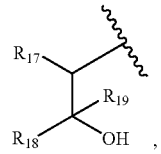

where $R_{17}$=$R_{18}$=$R_{19}$=H

In a further embodiment the following compounds are excluded:

(i) when $R_2$ or $R_5$=O-mycaminose (ii) when $R_2$ or $R_5$=O-angolosamine

In a preferred embodiment, the present invention provides novel compounds according to formula I:

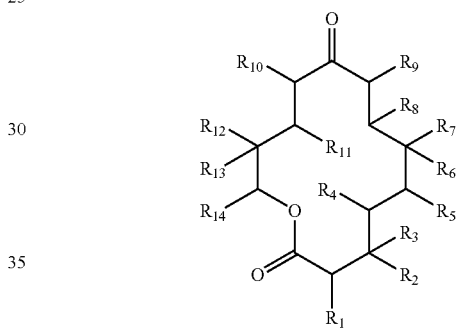

Where $R_1$=$R_4$=$R_6$=$R_9$=$R_{10}$=$R_{12}$=CH$_3$, $R_2$=OH, O-rhamnose and methylated derivatives thereof (2'-O methyl,2',3'-bis or 2',3',4'-tris-O-methyl), O-digitoxose, O-olivose, O-oliose or O-oleandrose, $R_3$=H, $R_5$=OH, O-mycaminose or O-angolosamine;

$R_7$=H, OH; $R_8$=H, OH, OCH$_3$; $R_{11}$=H, OH; $R_{13}$=H, OH; $R_{14}$=

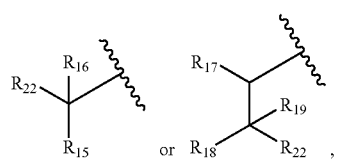

or where: $R_{15}$=H, CH$_3$, or CH$_2$CH$_3$ and $R_{16}$ is H; or $R_{17}$ and $R_{18}$ are each independently H or CH$_3$; $R_{19}$ is H and $R_{22}$ is OH. In a preferred embodiment $R_2$ and/or $R_5$ is not O-mycaminose or $R_2$ and/or $R_5$=O-angolosamine.

In a more highly preferred embodiment, the present invention provides novel compounds according to formula I:

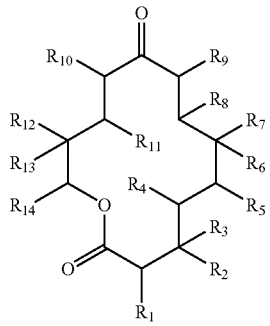

Where
$R_1=R_4=R_6=R_9=R_{10}=R_{12}=CH_3$, $R_2=OH$, O-rhamnose and methylated derivatives there of (2'-O methyl, 2',3'-bis or 2',3',4'-tris-O-methyl), O-digitoxose, O-olivose, O-oliose or O-oleandrose; $R_3=H$; $R_5=OH$, O-mycaminose or O-angolosamine; $R_7=H$, OH; $R_8=H$, OH, $OCH_3$; $R_{11}=H$, OH; $R_{13}=H$, OH; $R_{14}=$

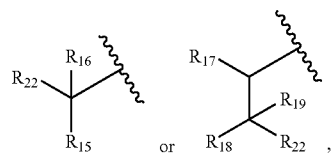

where: $R_{15}=CH_3$; $R_{16}$ is H; or $R_{17}=R_{18}=R_{19}=H$ and $R_{22}$ is OH. In a preferred embodiment $R_2$ and/or $R_5$ is not O-mycaminose or $R_2$ and/or $R_5=$O-angolosamine.

No stereochemistry is shown in Formula I as all possibilities are covered, including "natural" stereochemistries (as shown elsewhere in this specification) at some or all positions.

It may also be beneficial to clone and express the cytochrome P450 capable of hydroxylating the starter unit region of a 14-membered aglycone in an alternative host. For example, it may be beneficial to express the cytochrome P450 in a neutral host and feed the aglycone to this engineered host instead of the original host. This may have advantages because of the doubling time of the organism, ease of media preparation or for reasons to do with downstream processing. It may allow the cytochrome P450 to be placed under a known promoter or to allow the cytochrome P450 to be overexpressed in a host (for example *E. coli*) and purified and used in vitro or used by attaching the protein to a solid support.

It will also be understood by those skilled in the art that sometimes it will be beneficial to produce strains that can be fermented to directly produce the 14- or 15-hydroxy aglycone directly. Production of such strains reduces the numbers of steps such as fermentation, chemical isolation or structural characterisation required and may significantly reduce the cost of production of these molecules at large scale. Thus in a specific embodiment of this invention we consider the production of a strain that is capable of producing the desired hydroxylated aglycones by expression of a cytochrome P450 capable of hydroxylating the starter unit region of the aglycone in a strain producing either the aglycone or the glycosylated equivalent macrolide. As an example of how this might be done (example 9) we demonstrate the cloning of a cytochrome P450 from the lankamycin biosynthetic gene cluster. The gene cluster responsible for the production of lankamycin appears to contain a cytochrome P450 that has the ability to hydroxylate the 2-methyl butyrate starter unit that is used by this strain for the biosynthesis of lankamycin. Before this work it was not known whether this cytochrome P450 acted before or after the glycosylation of lankamycin but based on the evidence available a person of skill in the art would have assumed that the hydroxylation step occurred post-glycosylation in a manner similar to that seen previously. Additionally, it was not known that this cytochrome P450 could act on erythronolide B, the precursor to erythromycin. This cytochrome P450 was cloned from *S. rochei* ATCC21250 utilising the published partial PKS gene sequence from *S. rochei* as a probe (Suwa et al., Gene (2000) 246, 123-131). The gene encoding the cytochrome P450 was placed under the control of a promoter and expressed in *S. erythraea* DM which is an EB producer (Gaisser et al., Mol. Microbiol. (2000) 36, 391-401). The resulting strain was grown under standard conditions. Extracts of this strain were shown to contain hydroxyated EB. In this case the strain unexpectedly produced significant amounts of unmodified EB. However, it is known to those skilled in the art that a better matching of the timing of the expression of the introduced cytochrome P450 and the production of the EB substrate could result in greater production levels of the desired 15-hydroxy EB product. In addition the co-expression of the cognate ferredoxin/ferrodoxin reductase system for the introduced cytochrome P450 might also increase its catalytic efficiency.

In a further embodiment of this aspect of the invention the lankamycin cytochrome P450 was expressed in the wild type *S. erythraea* strain. The resulting strain was grown under standard conditions and extracted. Extracts of the strain were shown to produce a small proportion of 15-hydroxyerythromycin B, although it is likely that levels of the A form could be increased utilising the methods described earlier to upregulate eryK. This system produced significant amounts of erythromycin A which is naturally produced by this strain. Clearly, in this case the cytochrome P450 is less able to compete with the glycosyl transferase EryBV for their substrate, EB. A number of methods can be envisaged to increase the proportion of 15-hydroxy erythromycins produced by this strain. Firstly, increasing the catalytic efficiency of the cytochrome P450 by the methods described above. Secondly, by controlling the activity of the subsequent glycosylation steps until a greater proportion of the EB produced by the strain has been hydroxylated at the C15 position, for example by placing the eryBV gene under the control of an inducible promoter to allow the expression to be delayed until the hydroxylation of the starter unit region was complete.

Production levels of hydroxylated EB or hydroxylated erythromycins produced by this type of methodology might also be increased by selection of a cytochrome P450 that displays a greater preference for the erythronolide than the cloned *S. rochei* lankamycin cytochrome P450. Co-expression of their cognate ferredoxin/ferrodoxin reductase systems may also result in greater yields. Methods are known to those skilled in the art that will enable a skilled researcher to sample the complement of cytochromes P450 encoded by the genome of a cell. For example, it is possible to design degenerate oligo primers across conserved regions of a cytochrome P450 that enable the amplification of a range of cytochromes P450 from genomic DNA. It may be necessary to trial a range of degenerate oligo primers to adequately sample the entire range potentially expressed in the cell. If such an approach does not identify a cytochrome P450 that is capable of hydroxylating the starter unit region of an erythronolide it may also be possible to purify the activity using conventional protein biochemistry techniques. Recently the entire genome sequence of *S. avermitilis* has been published (Omura et al., PNAS (2001) 98, 12215-12220). Encoded in this genome are the gene sequences of 33 cytochromes P450. Our experiments have demonstrated that one of these cytochromes is capable of hydroxylating EB at the 15-position. It will be understood by those skilled in the art that it would be a relatively simple experiment to amplify each of these genes by polymerase chain reaction and test their ability to hydroxylate EB, thus determining exactly which of these cytochromes in this strain is responsible for the observed activity. Again it may be necessary to coexpress the cognate ferredoxin/ferrodoxin reductase system to maximise activity. Such expression studies could be conducted in an actinomycete host as described previously although it may also be possible to select an alternative host for example *E. coli*.

EXAMPLES

Example 1

Production of Erythronolide B

Figure 1:
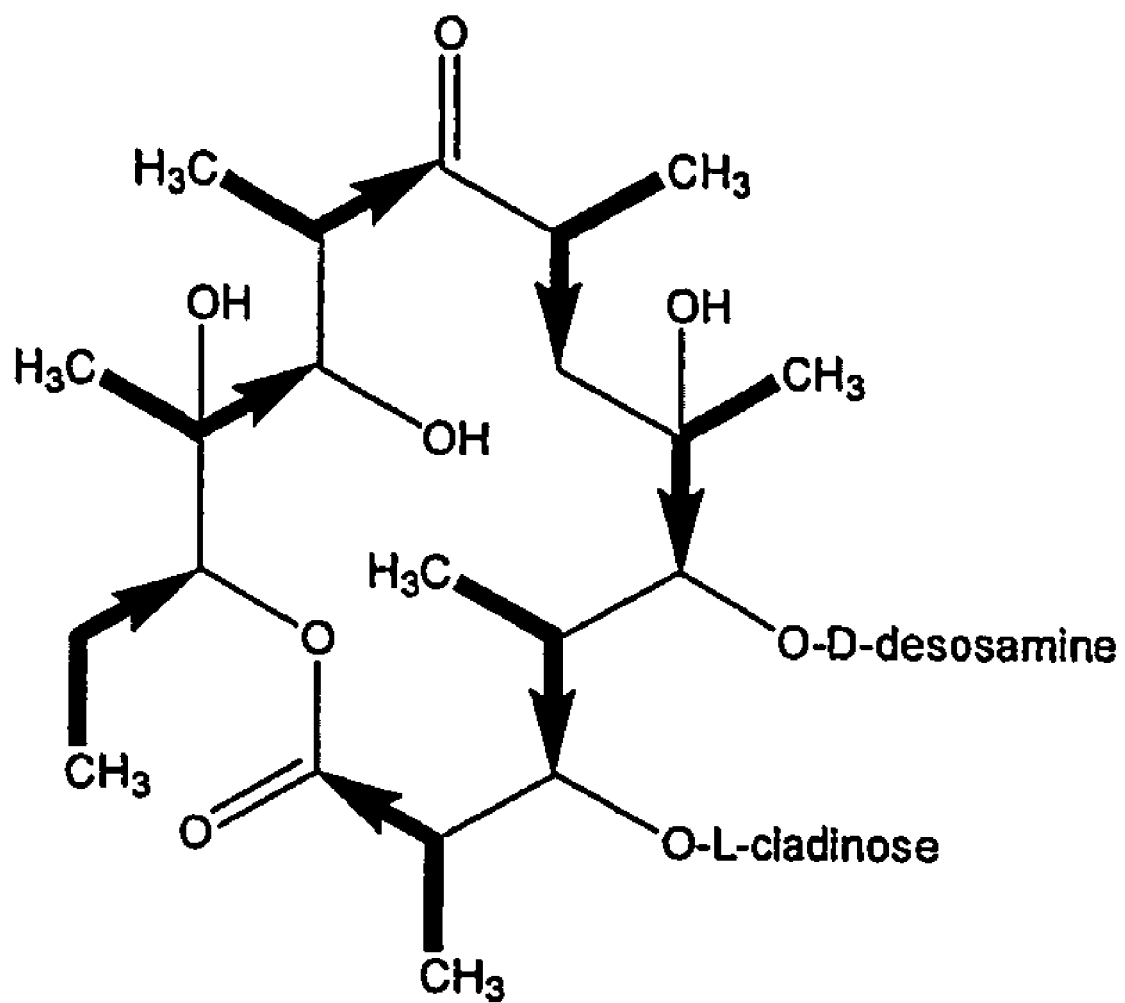
FIG. 1: shows how erythromycin is assembled from basic ketide units.

Erythronolide B was produced by fermentation of strain *S. erythraea* DM (Gaisser et al., Mol. Microbiol. (2000) 36, 391-401). *S. erythraea* DM was cultured from a frozen vegetative working stock (1:1, TSB culture:cryopreservative; TSB—Tryptic soy broth (Difco) 30 g/L, cryopreservative was 20% glycerol:10% lactose w/v in distilled water). A primary pre-culture was grown in TSB (50 ml in 250 ml flask) shaken at 250 rpm and 30° C. After two days this was used to inoculate (5% v/v) a secondary pre-culture of TSB (400 ml in a 2 liter flask), which was cultured under the same conditions for a further two days. Twelve liters of Ery-P (EryP media comprises Dextrose 5%, Nutrisoy flour 3%, ammonium sulfate 0.3%, calcium carbonate 0.6%, sodium chloride 0.5%, pH 7.0) production medium was inoculated with the secondary pre-culture (5% v/v) and allowed to ferment in a 20 liter stirred bioreactor (Applikon) for five days at 30° C. with an aeration rate of 6 liters/min. Broth was adjusted to pH 4 and centrifuged to remove the cells (3500 rpm, 30 minutes, 10° C.). The supernatant was extracted twice with ethyl acetate, and the cells extracted with methanol:ethyl acetate (1:1). The organic phases were combined and dried in vacuo, to give a concentrated aqueous extract which was partitioned against ethyl acetate. The ethyl acetate layer was dried in vacuo to give a crude extract. Erythronolide B was crystallised from the crude extract with cold acetone. The erythronolide B produced was confirmed by LCMS analysis (m/z=425.5, $(M+Na)^+$) vs. an authentic sample and subsequently the structure was confirmed by nmr.

Example 2

Small Scale Production of 14- and 15-hydroxy EBs

*S. eurythermus* (DSM40014) was inoculated into 10 ml of TSB media in a 25 ml flask. The flask was incubated on a rotary shaker with agitation at 250 rpm at 30° C. After 24 hours of incubation 1.5 ml of the whole broth was inoculated into a flask containing 25 ml Angolo media in a 250 ml flask (Angolo media comprises Glucose 2%, Arkasoy 2.5%, Casamino acids 0.2%, potato starch 2%, corn steep solids 0.25%, calcium carbonate 0.7%, pH 7.2). The flask was incubated for 24 hours at 250 rpm, 30° C. After 24 hours of incubation the flask was fed with 1 mg Erythronolide B in 100 μl methanol and incubated for a further 72 hours. At this time 1 ml of culture was removed and extracted twice with 0.5 ml of ethyl acetate. The combined extracts were evaporated to dryness. The residues were dissolved in methanol and analysed by LCMS. Two close running polar peaks could be identified with m/z=441.5, $(M+Na)^+$ consistent with the mass expected of a hydroxylated erythronolide B.

Example 3

Larger Scale Production of 14- and 15-hydroxy EBs

*S. eurythermus* (DSM40014) was inoculated into 10 ml of TSB media in a 25 ml-unbaffled flask. The flask was incubated on a rotary shaker with agitation at 250 rpm at 30° C. After 24 hours of incubation 1.5 ml of the whole broth was inoculated into a flask containing 25 ml Angolo media in a 250 ml-unbaffled flask. The flask was incubated for 24 hours at 250 rpm, 30° C. After 24 hours of incubation the flask was fed with 20 mg Erythronolide B in 100 μl methanol and incubated for a further 72 hours. At this time 1 ml culture was removed and extracted twice with 0.5 ml of ethyl acetate. The combined extracts were evaporated to dryness. The residues were dissolved in methanol and analyzed by LCMS. Again 2 polar peaks with m/z=441.5 $(M+Na)^+$ were identified consistent with that expected of a hydroxylated erythronolide B.

Example 4

Fermentation to Produce 14- and 15-hydroxy EB

A frozen vial (1 mL) of *S. eurythermus* (DSM40014) was inoculated into 50 mL of TSB media in a 250 ml-unbaffled flask. The flask was incubated on a rotary shaker with agitation at 250 rpm at 30° C. 10 ml of this culture was inoculated into each of 2×2 l unbaffled flasks containing 220 ml TSB media. The flasks were incubated on a rotary shaker with agitation at 250 rpm at 30° C. Approximately 200 ml of each culture was used to inoculate each of 2×4 l of Angolo media in an Applicon 7 l (working volume) stirred fermenter. The fermenters were stirred at between 500 and 900 rpm to maintain the maximal possible oxygenation during the fermentation. Drops of antifoam (SAG471) were added as required. After 24 hours each fermenter was fed with 2 grams erythronolide B in ~8 ml DMSO. The fermentation was continued for a further 48 hours and samples taken regularly to monitor for production of 14- and 15-hydroxy EB by LCMS and ELS.

Example 5

Purification of 14- and 15-hydroxy EB

Figure 2:
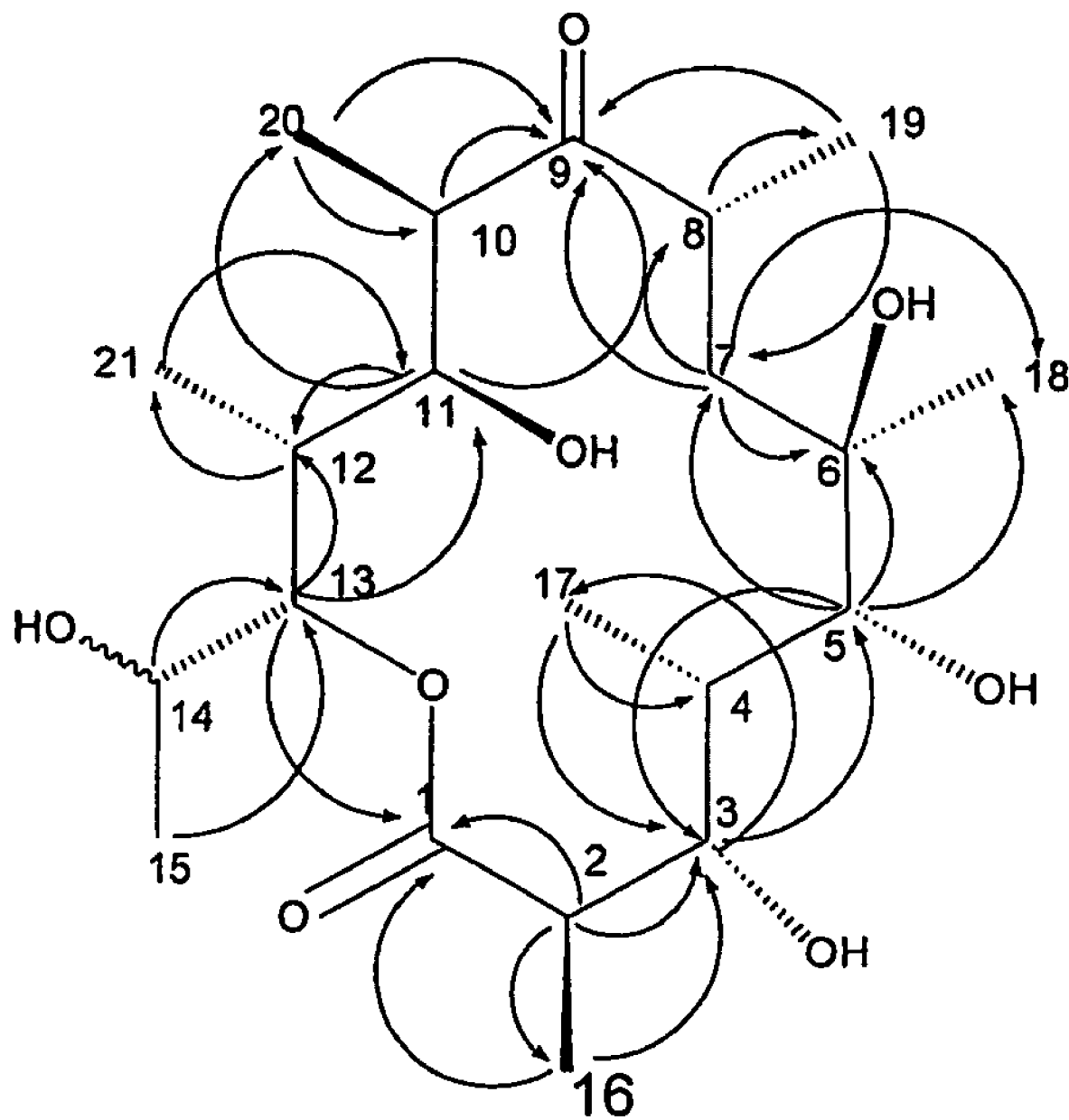
FIG. 2: shows the structure for the NMR of 14-hydroxy-erythronolide in $CD_3OD$.
Figure 3:
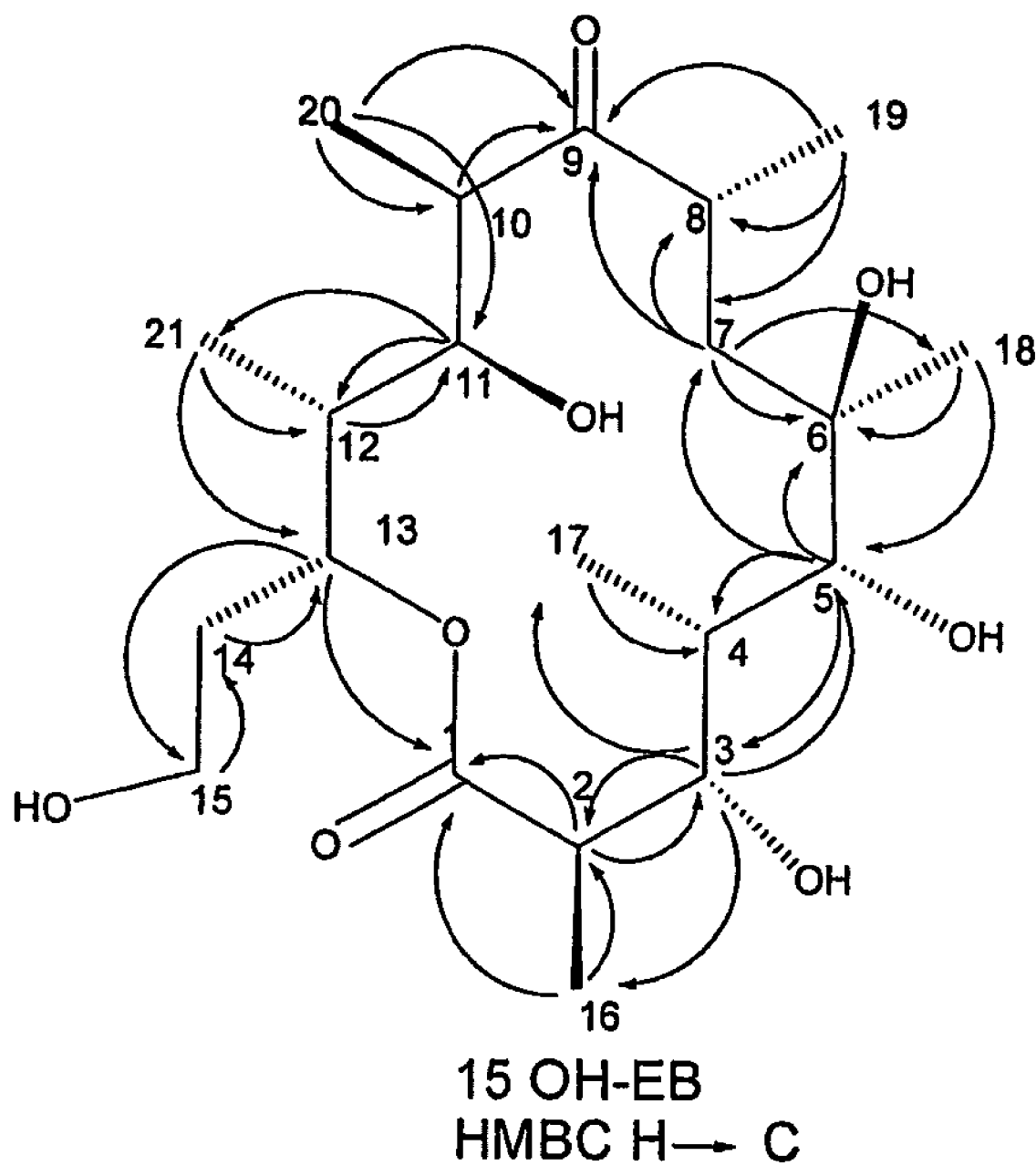
FIG. 3: shows the structure for the NMR of the 15-hydroxyerythronolide in $CD_3OD$.

The broth from one fermenter (~3.5 L) was centrifuged (3500 rpm, 30 minutes, 10° C.) to remove the cells. The supernatant was applied to a column of HP20 resin 20 cm diameter×15 cm height, washed with 2.5 l of water, then 2.5 l 100% methanol and finally 2.5 l 100% acetone. The hydroxylated EBs were found in the methanol fraction. The methanol fraction was dried in vacuo to give a crude extract. Both hydroxylated EBs were purified by silica chromatography (2.5 cm×30 cm). 14-Hydroxy EB was found to elute in 3% acetone in ethyl acetate and the 15-hydroxy EB eluted with 5-10% acetone in ethyl acetate. Purified hydroxylated compounds were analysed by LCMS and characterised structurally by nmr. Structural data are reported below. See also FIGS. 2 and 3.

NMR Data for 14-hydroxy Erythronolide B in $CD_3OD$.

| # |  | $\delta_C$ | $\delta_H$ (mult., Hz) | H—H COSY | H—C HMBC |
|---|---|---|---|---|---|
| 1 | O=C—O | 177.2 | | | |
| 2 | CH | 45.2 | 2.68 m | 3, 16 | 1, 3, 16 |
| 3 | CH—O | 80.2 | 3.57 (d, 10.5) | 2 | 5, 16, 17 |
| 4 | CH | 37.4 | 2.14 m | 5, 17 | |
| 5 | CH—O | 82.6 | 3.50 (d, 2.9) | 4 | 3, 6, 7, 18 |
| 6 | C—O | 75.9 | | | |
| 7 | $CH_2$ | 38.9 | 1.96 (dd, 14.7 9.3) | 7b, 8 | 6, 8, 9, 18 |
| | | | 1.37 (dd, 14.7, 4.1) | 7a, 8 | 6, 9, 18, 19 |
| 8 | CH | 45.5 | 2.70 m | 7a, 7b, 19 | |
| 9 | C=O | 220.5 | | | |
| 10 | CH | 41.3 | 3.04 (dq, 7.0, 1.2) | 11, 20 | 9 |
| 11 | CH—O | 71.1 | 3.92 (dd, 10.4, 1.3) | 10, 12 | 9, 12, 13, 20 |
| 12 | CH | 37.3 | 2.18 m | 11, 21 | 11, 21 |
| 13 | CH—O | 78.1 | 5.21 (dd, 9.1, 0.8) | 14 | 1, 12, 14, 15, 21 |
| 14 | CH—O | 66.8 | 3.80 (dq, 9.1, 6.3) | 13, 15 | 13 |
| 15 | $CH_3$ | 20.7 | 1.12 (d, 6.3) | 14 | 13, 14, |
| 16 | $CH_3$ | 15.3 | 1.18 (d, 6.7) | 2 | 1, 2, 3 |
| 17 | $CH_3$ | 8.1 | 0.99 (d, 8.0) | 4 | 3, 4 |
| 18 | $CH_3$ | 26.4 | 1.29 s | | 5, 7 |
| 19 | $CH_3$ | 18.4 | 1.13 (d, 7.8) | 8 | 7, 8, 9 |
| 20 | $CH_3$ | 9.3 | 0.97 (d, 7.0) | 10 | 9, 10, 11 |
| 21 | $CH_3$ | 9.8 | 0.95 (d, 7.1) | 12 | 11, 12, 14 |

NMR Data for 15-hydroxy Erythronolide B in $CD_3OD$

| # |  | $\delta_C$ | $\delta_H$ (mult., Hz) | H—H COSY | H—C HMBC |
|---|---|---|---|---|---|
| 1 | O=C—O | 177.5 | | | |
| 2 | CH | 45.2 | 2.68 (dm, 10.6) | 3, 16 | 1, 3, 16 |
| 3 | CH—O | 80.3 | 3.57 m | 2 | 2, 5, 16, 17 |
| 4 | CH | 37.4 | 2.13 (dd, 7.1, 1.3) | 5, 17 | |
| 5 | CH—O | 82.5 | 3.52 (d, 3.1) | 4 | 3, 4, 6, 7 |
| 6 | C—O | 75.9 | | | |
| 7 | $CH_2$ | 39.0 | 1.95 (dd, 14.8, 8.9) | 7b, 8 | 6, 8, 9 |
| | | | 1.38 (dd, 14.8, 4.4) | 7a, 8 | 8, 9, 18 |
| 8 | CH | 45.3 | 2.70 m | 7a, 7b, 19 | |
| 9 | C=O | 220.2 | | | |
| 10 | CH | 41.4 | 3.03 (dq, 6.7, 1.3) | 20 | 9 |
| 11 | CH—O | 71.3 | 3.95 (dd, 10.2, 1.3) | 12 | 12, 21 |
| 12 | CH | 42.1 | 1.65 m | 11, 21 | 11, 20, 21 |
| 13 | CH—O | 71.9 | 5.65 (dd, 9.9, 3.3) | 14a | 1, 15, 21 |
| 14 | $CH_2$ | 37.2 | 1.93 m | 13, 14b, 15 | 13 |
| | | | 1.70 m | 14a, 15 | |
| 15 | $CH_2$—O | 59.9 | 3.54 m | 14a, 14b | 14 |
| 16 | $CH_3$ | 15.4 | 1.18 (d, 6.7) | 2 | 1, 2 |
| 17 | $CH_3$ | 8.1 | 1.00 (d, 7.3) | 4 | 3, 4 |
| 18 | $CH_3$ | 26.4 | 1.28 s | | 5, 6, 7 |
| 19 | $CH_3$ | 18.3 | 1.14 (d, 7.0) | 8 | 7, 8, 9 |
| 20 | $CH_3$ | 9.8 | 0.96 (d, 6.7) | 10 | 9, 10, 11 |
| 21 | $CH_3$ | 9.2 | 0.97 (d, 6.7) | 12 | 12, 13, 14 |

Example 6

Biotransformation Using S. rochei at Small Scale to Give 15-hydroxy EB

A well growing culture of S. rochei ATCC21250 streaked on Bennett's agar was inoculated in 6 ml YEME media in a 25 ml flask (YEME comprises Difco yeast extract 0.3%, Difco Bacto peptone 0.5%, Difco malt extract 0.3%, glucose 1%, sucrose 34%). After 48 hours of incubation at 250 rpm and 30° C. the strain was subcultured (5%) into 30 ml YEME media in a 250 ml flask and incubated at 250 rpm, 30° C. for 24 hours. At this point the strain was fed with 2.2 mg EB and incubated for a further 5 days. A 1 ml sample was diluted 1:1 with methanol and analysed by LCMS. One polar peak with an m/z=441.5 $(M+Na)^+$ be identified. Further study showed this retention time was equivalent to that of an authentic sample of 15-hydroxy EB.

S. rochei ATCC21250 was inoculated into 30 ml YEME media in a 250 ml flask and incubated at 250 rpm, 30° C. for 48 hours. 10 ml was inoculated into 200 ml YEME media in a 2 l flask and incubated at 250 rpm, 30° C. for 48 hours. 200 ml of this culture was used to inoculate 4 l YEME media in a 7 l stirred fermenter (Applicon). The fermenter was stirred at between 500 and 700 rpm at 30° C. After 24 hours the culture was fed with 200 mg EB and fermented for a further 3-4 days. Samples were taken throughout the fermentation and analysed by LCMS and ELS for the presence of 15-hydroxy EB. 15-Hydroxy EB was isolated following the same methods of example 5.

Example 7

Production of 14- and 15-hydroxyerythromycins at Small Scale

The remainder of the culture from example 2 was extracted twice with ethyl acetate, the combined extracts were evaporated to dryness, dissolved in methanol and analysed by LCMS to confirm the presence of 14- and 15-hydroxy EB. Saccharopolyspora erythraea JC2 (Rowe et al., Gene (1998) 216, 25-223) was inoculated into 7 ml TSB (25 ml flask with spring) and shaken on a rotary shaker for 48 hours at 250 rpm, 30° C. 0.5 ml was used to inoculate 10 ml EryP media in a 25 ml flask (no spring) (EryP media comprises Dextrose 5%, Nutrisoy flour 3%, ammonium sulfate 0.3%, calcium carbonate 0.6% sodium chloride 0.5%, pH 7.0). After 24 hours the extract containing both 14- and 15-hydroxy EB was added and grown for a further 48 hours. A 1 ml sample was taken, adjusted to pH>9 and extracted twice with ethyl acetate. The combined extracts were evaporated to dryness, dissolved in methanol and analysed by LCMS. Two peaks m/z=734.5 $(M+H)^+$ consistent with the presence of 14- and 15-hydroxyerythromycin B were identified. Other desosamine containing peaks could also be identified.

Saccharopolyspora erythraea JC2 was inoculated into 7 ml TSB (25 ml flask with spring) and shaken on a rotary shaker for 48 hours at 250 rpm, 30° C. This culture was used to inoculate 30 ml EryP media in a 250 ml flask (no spring). At 48 hours purified 15-hydroxy EB (purified as described previously) was added and the fermentation continued for a further 48-72 hours. A 1 ml sample was taken, diluted 1:1 with acetonitrile and analysed by LCMS. New peaks of m/z=720.5, 734.5, 736.5 and 750.5 $(M+H)^+$ consistent with the presence of 15-hydroxy erythromycin D, B, C and A were identified.

Saccharopolyspora erythraea JC2 was inoculated into 7 ml TSB (25 ml flask with spring) and shaken on a rotary shaker for 48 hours at 250 rpm, 30° C. This culture was used to inoculate 30 ml EryP media in a 250 ml flask. At 48 hours purified 14-hydroxy EB (purified as described previously) was added and the fermentation continued for a further 48-72 hours. A 1 ml sample was taken, diluted 1:1 with acetonitrile and analysed by LCMS. New peaks of m/z=720.5, 734.5, 736.5 and 750.5 $(M+H)^+$ consistent with the presence of 14-hydroxyerythromycin D, B, C and A were identified.

Example 8

Production of 15-hydroxyerythromycin A by Enhancing eryK Action

To enhance the proportion of 15-hydroxyerythromycin A produced by the S. erythraea JC2 strain we placed eryK, the gene encoding the EryK cytochrome P450 responsible for the hydroxylation at C12 of erythromycin under the control of the actI/actIIorf4 promoter system. EryK was amplified by PCR using standard conditions and oligonucleotides that incorporated an NdeI site at the start codon and an XbaI site beyond the stop codon. The resulting amplified product was cloned into SmaI cut pUC18 and sequenced to ensure errors had not been introduced during the amplification process. The cytochrome P450-encoding insert was removed by digesting with NdeI and XbaI and ligated into pLSB2 (WO 03/070908) that had been digested with the same enzymes. The resulting plasmid was designated pSGK016; contained eryK under the control of the actI/actIIorf4 promoter system on an apramycin-based vector. This plasmid was used to transform S. erythraea JC2 using standard conditions; transformants were selected on R2T20 after 24 hours by overlaying with 100 µg/ml apramycin. The resulting strain was shown to have an enhanced ability to hydroxylate erythromycins at C12. This strain was inoculated into 7 ml TSB in a 25 ml flask containing a spring and 50 µg/ml apramycin and grown for 48 hours. At this point the strain was subcultured into 30 ml EryP media (5%) in a 250 ml flask with 50 µg/ml apramycin. At 48 hours the culture was fed with 15-hydroxy EB (50 mg/l) and grown for a further 48-72 hours. 1 ml samples were taken at regular intervals during this time. Samples were diluted 1:1 with acetonitrile and analysed by LCMS. Peaks corresponding to 15-hydroxyerythromycin A (m/z=750.5), (major), 15-hydroxyerythromycin B (m/z=734.5), 15-hydroxyerythromycin C (m/z=736.5) and 15-hydroxyerythromycin D (m/z=720.5), could be observed, all as $[M+H]^+$.

To further investigate the glycosylation of these compounds 100 µl of the samples were bioassayed. 250 ml melted 2TY agar was inoculated with an actively growing culture of M. luteus (NCIMB8553) and poured into a 24.3×24.3 cm square bioassay plate. Once the agar had set holes were punched in the agar and filled with 100%l of the 15-hydroxyerythromycins containing samples. Plates were incubated overnight at 37° C. Zones of inhibition were only observed with cultures that had been fed 15-hydroxy EB.

Example 9

Heterologous Expression of a Cytochrome P450

Genomic DNA from Streptomyces rochei ATCC21250 was used as a template together with the primers LankP450Nde 5'-CATATGAACCAGCCGCAACTGC-3' (SEQ ID NO: 1) and LankP450Xba 5'-TCTAGACCTCATGGACTCAC-CCCCA-3' (SEQ ID NO: 2) to amplify an about 1.2 kb DNA fragment encoding a cytochrome P450 monooxygenase. The fragment was cloned into pUC19 using standard techniques, followed by digestion with NdeI and XbaI for ligation of the insert fragment into the vector backbone of pSG144 constructed as below.

Plasmid pSG144 is a derivative of pSG142 (Gaisser et al., Mol. Microbiol. (2000) 36, 391-401) in which the XbaI site between the thiostrepton gene and the eryRHS (a neutral area used as homology for integration) has been removed by digestion of pSG142 with XbaI and filled in using standard protocols and religated to give pSG143. In addition, the His tag at the end of eryBV has been removed from pSG142 and replaced by an XbaI site at the end of eryBV. To replace the eryBV gene in this pSG142 vector with an eryBV gene with a XbaI site a series of intermediate vectors were constructed. PUC18eryBVcas was constructed by amplifying the gene eryBV by PCR using the primers casOIeG21 (WO01/79520) and 7966 5'-GGGGAATTCAGATCTGGTCTAGAGGTCAGCCGGCGTGGCGGCGCGTGAGTTCCTCCAGTCGCGGGACGATCT-3' (SEQ ID NO: 3) and pSG142 (Gaisser et al., Mol. Microbiol. (2000) 36, 391-401) as a template. The PCR fragment was cloned using standard procedures and plasmid pUC18eryBVcas isolated with an NdeI site overlapping the start codon of eryBV and XbaI and BglII sites following the stop codon. The construct was verified by sequence analysis. The gene eryBV was amplified by PCR using the primers BIOSG1 5'-GGGTCTAGATCCGGACGAACGCATCGATTAATTAAGGAGGACACATA-3' (SEQ ID NO: 4) and 7966 5'-GGGGAATTCAGATCTGGTCTAGAGG TCAGCCGGCGTGGCGGCGCGTGAGTTCCTCCAGTCGCGGGACGATCT-3' (SEQ ID NO: 3), which introduce an XbaI site sensitive to Dam methylation at the 5' end and an XbaI site and a BglII site at the 3' end of eryBV. Plasmid pUC18eryBVcas was used as a template. After treatment with T4 polynucleotide kinase using standard techniques the amplified product was ligated with SmaI cut pUC18 and used to transform E. coli DH10B. The construct was then digested using BamHI/BglII and an approximately 1.3 kb DNA band was isolated and cloned into Litmus 28 previously digested with BamHI/Bg/II using standard procedures. The vector pSGLit1 was isolated and the DNA sequence of the insert verified by sequence analysis. Plasmid pSGLit1 was digested with NdeI/Bg/II and an approximately 1.3 kb band isolated and cloned into pSG143 that had been digested with the same enzymes. The ligation was transformed into E. coli DH10B and the plasmid pSG144 verified by sequence analysis.

Plasmid pLSB150 was used to transform S. erythraea DM, a producer of the compound erythronolide B (Gaisser et al., Mol. Microbiol. (2000) 36, 391-401). Transformants were selected on R2T20 agar overlayered at 24 hours with 40 μg/ml thiostrepton. The resulting strain S. erythraea NRRL2338 DM/pLSB150 was grown in 7 ml TSB liquid media containing 5 μg/ml thiostrepton for 48 hours before being subcultured (5%) into 30 ml EryP media containing 5 μg/ml thiostrepton. Cultures were grown for a further 5-6 days before analysis. 1 ml culture supernatant was extracted three times with ethyl acetate. The combined organic layers were dried in vacuo and samples analysed by LCMS vs. a control sample of S. erythraea DM grown at the same time. The presence of a polar peak of m/z=441.5 [M+Na]$^+$ corresponding to hydroxylated EB was identified; thus demonstrating that this cytochrome P450 could act on the EB aglycone.

Plasmid pLSB150 was isolated using standard protocols and used to transform Saccharopolyspora erythraeaNRRL2338. Transformants were selected on R2T20 agar overlayered at 24 hours with 40 μg/ml thiostrepton. The resulting strains S. erythraea NRRL2338/pLSB150 were grown in 7 ml TSB liquid media containing 5 μg/ml thiostrepton for 48 hours before being subcultured (5%) into 30 ml EryP media containing 5 μg/ml thiostrepton. Cultures were grown for a further 5-6 days before analysis. 1 ml culture supernatant was brought to pH>9 and extracted three times with ethyl acetate. The combined organic layers were dried in vacuo and samples analysed by LCMS vs. a control sample of S. erythraea NRRL2338 grown at the same time. The presence of a polar peak of m/z=734.5 [M+H]$^+$ corresponding to hydroxylated erythromycin B could be observed in addition to the less polar erythromycin peaks normally observed during fermentation of S. erythraea.

Example 10

Addition of Alternative Sugars

S. erythraea JC2 ΔCIII was produced from strain JC2 (Rowe et al., Gene (1998) 216, 25-223) by transforming and subsequently resolving the plasmid used to make the chromosomal deletion of eryCIII (Gaisser et al., Mol. Microbiol. (2000) 36, 391-401). The strain S. erythraea JC2 ΔCIII retains the ability to transfer the mycarose sugar to the C-3 hydroxy group of erythronolides. S. erythraea JC2 ΔCIII was inoculated into 7 ml TSB in a 25 ml flask and grown for 48 hours at 30° C. and 250 rpm. At this time the strain was subcultured into 25 ml EryP media (5%) in a 250 ml flask and fermented at 30° C., 250 rpm. At 48 hours the cultures were fed at 50 mg/l 15-hydroxy EB and grown for a further 72 hours. Samples were taken at regular intervals, diluted with acetonitrile 1:1, centrifuged and analysed by LCMS. A peak of m/z=585.5 [M+Na]$^+$ could be identified consistent with the presence of 3-O-mycarosyl-15-hydroxy EB.

S. erythraea SGT2 pSGOLEG2 (Gaisser et al., Mol. Microbiol. (2000) 36, 391-401) was inoculated into inoculated into 7 ml TSB in a 25 ml flask and grown for 48 hours at 30° C. and 250 rpm. At this time the strain was subcultured into 25 ml EryP media (5%) in a 250 ml flask and fermented for 48 hours at 30° C. At 48 hours the cultures were fed at 50 mg/l 15-hydroxy EB and grown for a further 72 hours. Samples were taken at regular intervals, diluted 1:1 with acetonitrile, centrifuged and analysed by LCMS. Peaks of m/z=587.5 [M+Na]$^+$ and 585.5 [M+Na]$^+$ could be identified consistent with the presence of 3-O-rhamnosyl-15-hydroxy EB and 3-O-mycarosyl-15-hydroxy EB.

Example 12

Biotransformation of 15-hydroxyerythronolide B

S. erythraea JC2/ΔCIII (see supra) was inoculated into 200 ml TSB in a 2 L Erlenmeyer flask and incubated at 28° C. and 250 rpm. After 48 h the strain was sub-cultured into 4 liters of SSDM medium (5% v/v) and incubated for 48 h (SSDM media comprises per L: Sucrose, 69 g; Potassium nitrate, 10 g; Succinic acid, 2.63 g; $KH_2PO_4$, 2.7 g; $MgSO_4 \cdot 7H_2O$, 1.2 g; trace element solution 10 ml (g/L $ZnCl_2$, 1 g; $MnCl_2 \cdot 4H_2O$, 0.62 g; $CuCl_2 \cdot 2H_2O$, 0.053 g; $CoCl_2$, 0.055 g; $FeSO_4 \cdot 7H_2O$, 2.5 g; $CaCl_2 \cdot 2H_2O$, 3.8 g); adjusted to pH 6.2 with 1 M KOH). The cultures were then fed with 15-hydroxy EB (50 mg/L final concentration) and incubated for a further 88 h. To monitor the bioconversion samples were taken at regular Intervals, diluted 1:1 (v/v) with methanol, shaken for 10 min and then centrifuged and analysed by LC/ESI-MS.

Example 13

Purification of 3-O-mycarosyl-15-OH EB

The broth from one fermenter (approx. 3.5 liters) was centrifuged (3500 rpm, 30 min) and the supernatant was transferred to a column of HP20 resin (20 cm diameter×15 cm height). The resin was washed with water (2×2.5 liters) and methanol (2.5 liters) was used to elute 3-βmycarosyl-15-hydroxyerythronolide B. The organic fraction was dried under reduced pressure to give crude 3-O-mycarosyl-15-hydroxyerythronolide B. This extract was further purified by column chromatography over flash silica using ethyl acetate and subsequently ethyl acetate/methanol (v:v; 1:1) as eluants. Purification by HPLC using a reversed phase $C_{18}$-column and eluting with water/acetonitrile (v:v, 70:30) gave 3-O-mycarosyl-15-hydroxyerythronolide B as a colourless solid.

NMR Data for 3-O-mycarosyl-15-OH EB in $CD_3OD$

| # | | $\delta_c$ | $\delta_H$ (mult, Hz) | H—H COSY | H—C HMBC |
|---|---|---|---|---|---|
| 1 | O=C—O | 176.72 | | | |
| 2 | CH | 45.87 | 2.84 (m) | 3, 16 | 16, 4, 3, 1 |
| 3 | CH—O | 87.94 | 3.72 (dd, 1.0, 9.9) | 2, 4 | 17, 16, 4, 2, 5, 1, 1' |
| 4 | OH | 37.77 | 2.12 (m) | 3, 5, 17 | 17, 6, 5 |
| 5 | CH—O | 81.58 | 3.52 (m) | 4 | 3, 4, 6, 8 |
| 6 | C—O | 75.83 | | | |
| 7α | $CH_2$ | 38.18 | 1.41 (dd, 3.1, 14.7) | 7β, 8 | 9, 18, 19 |
| 7β | | 38.18 | 1.92 (m) | 7α, 8 | 6, 8, 18 |
| 8 | CH | 46.01 | 2.70 (m) | 7α, 7β, 19 | 7, 9, 19 |
| 9 | C=O | 220.49 | | | |
| 10 | CH | 41.22 | 3.01 (dq, 1.4, 6.8) | 11, 20 | 9, 11, 20 |
| 11 | CH—O | 71.10 | 3.92 (dd, 1.4, 10.2) | 10, 12 | 9, 10, 13, 21 |
| 12 | CH | 42.00 | 1.62 (m) | 11, 21 | 11, 21 |
| 13 | CH—O | 72.03 | 5.62 (dd, 3.3, 9.9) | 12, 14α | 1, 11, 12, 14, 15, 21 |
| 14α | $CH_2$ | 37.20 | 1.92 (m) | 13, 14β, 15 | 1, 12, 13, 15 |
| 14β | | 37.20 | 1.67 (m) | 13, 14α, 15 | 15 |
| 15 | $CH_2$—O | 60.01 | 3.52 (m) | 14α, 14β | 13, 14 |
| 16 | $CH_3$ | 15.83 | 1.16 (d, 6.9) | 2 | 1, 2, 3 |
| 17 | $CH_3$ | 9.21 | 1.00 (d, 7.2) | 4 | 3, 4, 5 |
| 18 | $CH_3$ | 26.47 | 1.30 (s) | | 5, 6, 7 |
| 19 | $CH_3$ | 18.87 | 1.12 (d, 7.0) | 8 | 7, 8, 9 |
| 20 | $CH_3$ | 9.88 | 0.94 37d 6.8) | 10 | 9, 10, 11 |
| 21 | $CH_3$ | 9.56 | 0.95 (d. 7.1) | 12 | |
| 1' | O—C—O | 100.76 | 4.99 (pd, 4.0) | 2'α, 2'β | 3, 3', 5' |
| 2'α | $CH_2$ | 42.24 | 1.82 (dd, 4.0, 14.5) | 1', 2'β | 1', 3' |
| 2'β | $CH_2$ | 42.24 | 2,05 (pd, 14.5 Hz) | 1', 2'α | 1', 3', 4', 7' |
| 3' | C—O | 71.10 | | | |
| 4' | CH—O | 77.75 | 2.96 (d, 9.8) | 5' | 3', 5', 6', 7' |
| 5' | CH | 66.90 | 4.04 (dq, 6.1, 9.8) | 4', 6' | 3', 4', 6' |
| 6' | $CH_3$ | 18.41 | 1.26 (d, 6.1 Hz) | 5' | 4', 5' |
| 7' | $CH_3$ | 26.20 | 1.20 (s) | | 2', 3', 4' |

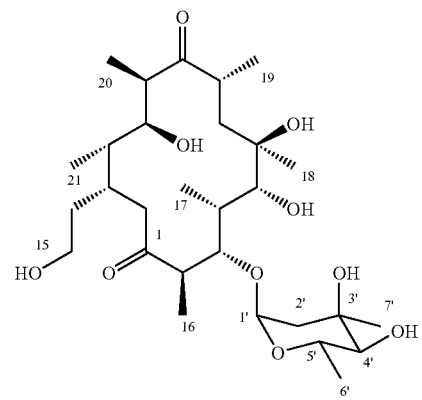

The invention claimed is:

1. A compound according to formula I below:

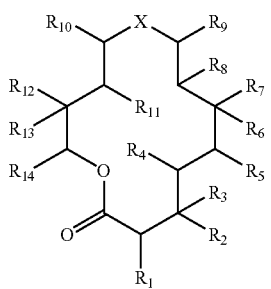

I wherein $X = -C(=O)-$, $-CH(OH)-$ or $-CH_2-$, $R_1$, $R_4$, $R_6$, $R_9$, $R_{10}$ and $R_{12}$ are each independently H, $CH_3$ or $CH_2CH_3$, $R_2$=OH or a glycosyl group selected from the group consisting of O-cladinose, O-mycarose, O-rhamnose, 2'-O-methyl rhamnose, 2',3'bis-O-methyl rhamnose, 2',3',4'-tris-O-methyl rhamnose, O-digitoxose, O-olivose, O-oliose, O-oleandrose, O-mycaminose, and O-angolosamine; $R_3$=H, or $R_2$ and $R_3$ together are keto; $R_5$=OH or a glycosyl group selected from the group consisting of O-mycarose, O-rhamnose, 2'-O-methyl rhamnose, 2',3'-bis-O-methyl rhamnose, 2',3',4'-tris-O-methyl rhamnose, O-digitoxose, O-olivose, O-oliose, O-oleandrose, O-desosamine, O-mycaminose, and O-angolosamine; $R_7$=H or OH; $R_8$=H or OH;

$R_{11}$=H or OH, $R_{13}$=H or OH, $R_{14}$=

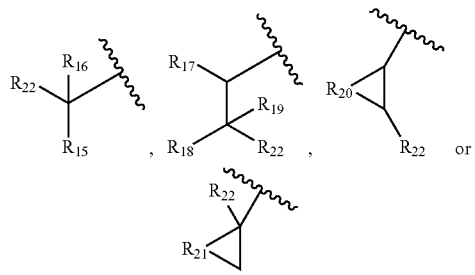

where: $R_{15}$ is H or a $C_1$-$C_7$ alkyl group or $C_4$-$C_7$ cycloaklyl group; $R_{16}$ is H, a $C_1$-$C_7$ alkyl group or $C_4$-$C_7$ cycloaklyl group, $R_{17}$, $R_{18}$ and $R_{19}$ are each independently H or a $C_1$-$C_7$ alkyl group or $R_{20}$ or $R_{21}$ are $(CH_2)_x$, where x=2-5 and $R_{22}$ is O—$R_{23}$ where $R_{23}$=H or a $C_1$ to $C_7$ alkyl group or $C_1$-$C_7$ acyl group; or $R_{22}$ and $R_{16}$ together are a keto group; or $R_{22}$ and $R_{19}$ together are a keto group; with the proviso that the following compounds are excluded:
(a) when $R_2$=OH, O-cladinose or O-mycarose and $R_5$ is OH or O-desosamine
(b) when $R_1$=$R_4$=$R_6$=$R_9$=$R_{10}$=$R_{12}$=$CH_3$, $R_3$=H, $R_2$=O-oleandrose, $R_5$=O-desosamine, $R_7$=OH, $R_8$=$R_{13}$=H and $R_{14}$=

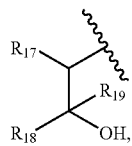

where $R_{17}$=$R_{18}$=$R_{19}$=H,
(c) when $R_2$ or $R_5$=O-mycaminose
(d) when $R_2$ or $R_5$=O-angolosamine.

2. A compound according to claim 1 wherein $R_2$ is selected from the group consisting of O-cladinose, O-mycarose, O-rhamnose, 2'-O-methyl rhamnose, 2',3'-bis-O-methyl rhamnose, 2',3',4'-tris-O-methyl rhamnose, O-digitoxose, O-olivose, O-oliose and O-oleandrose.

3. A compound according to claim 2 wherein $R_2$ is selected from the group consisting of 2'-O-methyl rhamnose, 2',3'-bis-O-methyl rhamnose and 2',3',4'-tris-O-methyl rhamnose.

4. A compound according to claim 1, wherein $R_5$ is a glycosyl group selected from O-mycaminose and O-angolosamine.

5. A compound according to claim 1, where X=—C(=O)—, $R_1$=$R_4$=$R_6$=$R_9$-$R_{10}$=$R_{12}$=$CH_3$, $R_2$=OH, O-rhamnose, 2'-O-methyl rhamnose, 2',3'-bis-O-methyl rhamnose, 2',3',4'-tris-O-methyl rhamnose, O-digitoxose, O-olivose, O-oliose or O-oleandrose, $R_3$=H, $R_5$=OH, O-mycaminose or O-angolosamine; $R_7$=H or OH; $R_8$=H or OH; $R_{11}$=H or OH; $R_{13}$=H or OH; $R_{14}$=

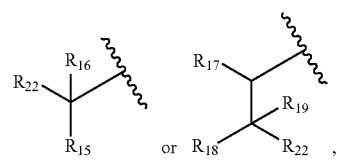

where: $R_{15}$=H, $CH_3$, or $CH_2CH_3$ and $R_{16}$ is H; or $R_{17}$ and $R_{18}$ are each independently H or $CH_3$; $R_{19}$ is H and $R_{22}$ is OH.

6. A compound according to claim 5, where X=—C(=O)—, $R_1$=$R_4$=$R_6$=$R_9$=$R_{10}$-$R_{12}$=$CH_3$, $R_2$=OH, O-rhamnose, 2'-O-methyl rhamnose, 2',3'-bis-O-methyl rhamnose, 2',3',4'-tris-O-methyl rhamnose, O-digitoxose, O-olivose, O-oliose or O-oleandrose; $R_3$=H; $R_5$=OH, O-mycaminose or O-angolosamine; $R_7$=H or OH; $R_8$=H or OH; $R_{11}$=H or OH; $R_{13}$=H or OH; $R_{14}$=

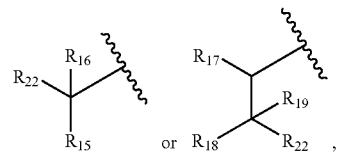

where: $R_{15}$=$CH_3$; $R_{16}$ is H; or $R_{17}$=$R_{18}$=$R_{19}$=H and $R_{22}$ is OH.

* * * * *

UNITED STATES PATENT AND TRADEMARK OFFICE
CERTIFICATE OF CORRECTION

| | | |
|---|---|---|
| PATENT NO. | : 7,807,800 B2 | Page 1 of 1 |
| APPLICATION NO. | : 10/580781 | |
| DATED | : October 5, 2010 | |
| INVENTOR(S) | : Kendrew et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 434 days.

Signed and Sealed this
Nineteenth Day of July, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 22
<212> TYPE: DNA
<213> ORGANISM: Artificial sequence
<220> FEATURE:
<223> OTHER INFORMATION: Primer

<400> SEQUENCE: 1
catatgaacc agccgcaact gc                                              22

<210> SEQ ID NO 2
<211> LENGTH: 25
<212> TYPE: DNA
<213> ORGANISM: Artificial sequence
<220> FEATURE:
<223> OTHER INFORMATION: Primer

<400> SEQUENCE: 2
tctagacctc atggactcac cccca                                           25

<210> SEQ ID NO 3
<211> LENGTH: 72
<212> TYPE: DNA
<213> ORGANISM: Artificial sequence
<220> FEATURE:
<223> OTHER INFORMATION: Primer

<400> SEQUENCE: 3
ggggaattca gatctggtct agaggtcagc cggcgtggcg gcgcgtgagt tcctccagtc     60
gcgggacgat ct                                                         72

<210> SEQ ID NO 4
<211> LENGTH: 47
<212> TYPE: DNA
<213> ORGANISM: Artificial sequence
<220> FEATURE:
<223> OTHER INFORMATION: Primer

<400> SEQUENCE: 4
gggtctagat ccggacgaac gcatcgatta attaaggagg acacata                   47